United States Patent
Eggenweiler et al.

(10) Patent No.: US 7,312,224 B2
(45) Date of Patent: Dec. 25, 2007

(54) PYRIMIDINE DERIVATIVES

(75) Inventors: Hans-Micahel Eggenweiler, Darmstadt (DE); Manfred Baumgarth, Darmstadt (DE); Pierre Schelling, Muehltal (DE); Norbert Beier, Reinheim (DE); Maria Christadler, Roedermark (DE)

(73) Assignee: Merck Patent GmbH, Darmstadt (DE)

( * ) Notice: Subject to any disclaimer, the term of this patent is extended or adjusted under 35 U.S.C. 154(b) by 438 days.

(21) Appl. No.: 10/491,680

(22) PCT Filed: Sep. 4, 2002

(86) PCT No.: PCT/EP02/09935

§ 371 (c)(1),
(2), (4) Date: Apr. 2, 2004

(87) PCT Pub. No.: WO03/031447

PCT Pub. Date: Apr. 17, 2003

(65) Prior Publication Data
US 2004/0242595 A1 Dec. 2, 2004

(30) Foreign Application Priority Data
Oct. 4, 2001 (DE) ................................ 101 48 883

(51) Int. Cl.
A01N 43/54 (2006.01)
A61K 31/505 (2006.01)
C07D 239/00 (2006.01)
C07D 471/00 (2006.01)
C07D 487/00 (2006.01)
C07D 491/00 (2006.01)

(52) U.S. Cl. ........................ 514/267; 544/250
(58) Field of Classification Search ............ 514/258.1; 544/280, 278
See application file for complete search history.

(56) References Cited

U.S. PATENT DOCUMENTS 3,037,980 A * 6/1962 Hitchings et al. .......... 544/280
4,007,187 A 2/1977 Fauran et al.

FOREIGN PATENT DOCUMENTS

| EP | 0 046 677 | 3/1982 |
|---|---|---|
| EP | 0 514 540 | 11/1992 |
| EP | 0 728 759 | 8/1996 |
| WO | 98 17668 | 4/1998 |
| WO | 99 28325 | 6/1999 |
| WO | 99 55708 | 11/1999 |
| WO | 99 62518 | 12/1999 |
| WO | WO 99 62518 A * | 12/1999 |
| WO | 01 18004 | 3/2001 |
| WO | 01 21620 | 3/2001 |
| WO | 01 39777 | 6/2001 |
| WO | WO 01/39777 A1 * | 6/2001 |
| WO | 02 057267 | 7/2002 |

OTHER PUBLICATIONS

West, Anthony R., Solid State Chemistry and Its Applications, Wiley, New York (1988).*
Meade, et al., Anxiolytic Activity of Analogues of 4-benzylamino-2-methyl-7H-pyrrolo[2,3-d]pyrimidines, Eur. J. Med. Chem., pp. 363-374, vol. 33 (1998).*
Campbell, et al., Selective A1-adenosine Receptor Antagonists Identified Using Yeast *Saccharomyces cerevisiae* Functional Assays, Bioorganic & Medicinal Chemistry Letters, 9, 2413-2418 (1999).*
Chemical Abstracts No. 48031, vol. 80, No. 9 (Mar. 4, 1974).
Chemical Abstracts No. 82224, vol. 82, No. 13 (Mar. 31, 1975).
Chemical Abstracts No. 126924, vol. 76, No. 21 (May 22, 1972).
Chemical Abstracts, vol. 63, No. 11 (1965).
Chemical Abstracts No. 97174, vol. 111, No. 11 (Sep. 11, 1989).
Chemical Abstracts No. 112617, vol. 123, No. 9 (Aug. 28, 1995).
Chemical Abstracts No. 79191, vol. 83, No. 9 (Sep. 1, 1975).
R. Campbell, et al., "Selective A1-Adenosine Receptor . . . Functional Assays", *Bioorganic & Medicinal Chemistry Letters*, Bd. 9, Nr. 16 (Aug. 16, 1999).
E. Meade, et al., "Anxiolytic Activity . . . pyrimidines", *European Journal of Medicinal Chemistry*, Bd. 33, Nr. 5, (Jun. 1, 1998).
West, et al., "2-Alkyl(aryl) . . . pyrimidines", *J. Org. Chem*, Bd. 26 (1961).
Lockhart et al., "Synthesis of Subtituted furo . . . ", *J. Heterocyclic Chem*, Bd. 33, Nr. 3 (1996).
J-P Marquet et al., "Furannes et Pyrroles . . . 4-Substitut", *Bulletin de la Societe Chimique de France*, Nr. 12 (1969).

* cited by examiner

Primary Examiner—James O. Wilson
Assistant Examiner—Erich A. Leeser
(74) Attorney, Agent, or Firm—Millen, White, Zelano & Branigan, P.C.

(57) ABSTRACT

Pyrimidine derivatives of the formula (I) and physiologically acceptable salts thereof, in which $R^1$, $R^2$, $R^3$, $R^4$, W, X, Y and Z are as defined in claim 1, exhibit phosphodiesterase V inhibition and can be employed for the treatment of diseases of the cardiovascular system and for the treatment and/or therapy of potency disorders

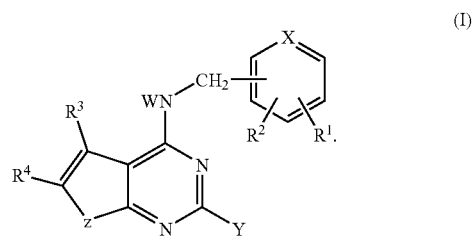

20 Claims, No Drawings

PYRIMIDINE DERIVATIVES

The invention relates to compounds of the formula I

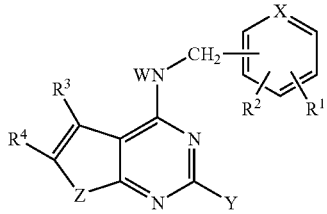

in which
R$^1$ and R$^2$ are each, independently of one another, H, A, OH, OA or Hal,
R$^1$ and R$^2$ together are alternatively alkylene having 3-5 carbon atoms, —O—CH$_2$—CH$_2$—, —CH$_2$—O—CH$_2$—, —O—CH$_2$—O— or —O—CH$_2$—CH$_2$—O—,
R$^3$ and R$^4$ are each, independently of one another, H, A or Hal,
R$^3$ and R$^4$ together are alternatively alkylene or alkylidene having 3-5 carbon atoms, or

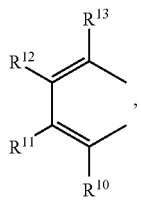

W is H or alkyl having 1, 2, 3 or 4 carbon atoms,
X is CH or N,
Y is (CH$_2$)$_q$—R$^7$ or R$^5$, R$^6$ or R$^9$, each of which is unsubstituted or monosubstituted by (CH$_2$)$_n$R$^{20}$,
Z is O, NH or NA',
A' is alkyl having 1-6 carbon atoms, —CHAr or —CHAr-A'',
A'' is alkyl having 1-6 carbon atoms,
R$^5$ is linear or branched alkyl having 1-10 carbon atoms, in which one or two CH$_2$ groups may be replaced by —CH═CH— groups, —C≡C— groups, —O—, CO, —S—, —SO—, SO$_2$, —NH— or —NA-,
R$^6$ is cycloalkyl or cycloalkylalkylene having 5-12 carbon atoms,
R$^7$ is a saturated or unsaturated 5-7-membered heterocyclic radical having 1-4 N, O or S atoms which is unsubstituted or monosubstituted, disubstituted or trisubstituted by R$^{20}$, A, Hal or CF$_3$,
R$^9$ is Ar or (CH$_2$)$_k$—Ar,
R$^{10}$, R$^{11}$,
R$^{12}$ and R$^{13}$ are each, independently of one another, H, A, Hal, OA, OH, NH$_2$, NHA, NA$_2$ or R$^{20}$,
R$^{20}$ is —COOH, —COOA, —CONH$_2$, —CONHA, —CONA$_2$, —CN, tetrazol-5-yl, —S(O)$_m$A, —S(O)$_m$NH$_2$ or —S(O)$_m$OH,

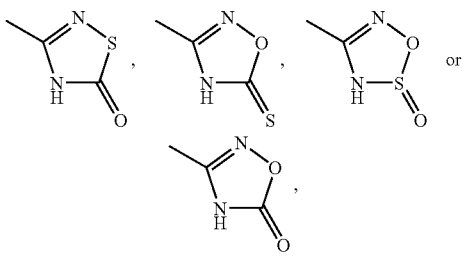

A is alkyl or alkenyl having from 1 to 6 carbon atoms, in which 1-7 H atoms may be replaced by F,
Ar is a phenyl radical which is unsubstituted or monosubstituted, disubstituted or trisubstituted by Hal, A, OA, OH, SO$_2$NH$_2$, SO$_2$NHA, SO$_2$NA$_2$ or CN,
Hal is F, Cl, Br or I,
k and q are each, independently of one another, 0, 1, 2, 3 or 4,
m is 1 or 2 and
n is 0, 1, 2 or 3, and pharmaceutically usable derivatives, solvates and stereoisomers thereof, including mixtures thereof in all ratios.

Pyrimidine derivates are disclosed, for example, in EP 0920431, EP 0934321, WO 99/28325, WO 99/55708, WO 00/78767 and WO 01/21620.

The invention had the object of finding novel compounds having valuable properties, in particular those which can be used for the preparation of medicaments.

It has been found that the compounds of the formula I and salts and/or solvates thereof have very valuable pharmacological properties and are well tolerated.

In particular, they exhibit specific inhibition of cGMP phosphodiesterase (PDE V).

Compared with the compounds from the prior art, the compounds according to the invention have more favourable physical/chemical properties. Thus, they have better solubility and are, for example, absorbed better on oral administration.

Quinazolines having a cGMP phosphodiesterase-inhibiting activity are described, for example, in J. Med. Chem. 36, 3765 (1993) and ibid. 37, 2106 (1994).

The biological activity of the compounds of the formula I can be determined by methods as described, for example, in WO 93/06104.

The affinity of the compounds according to the invention for cGMP and cAMP phosphodiesterase is determined by measuring their IC$_{50}$ values (concentration of the inhibitor needed to achieve 50% inhibition of the enzyme activity).

The determinations can be carried out using enzymes isolated by known methods (for example W. J. Thompson et al., Biochem. 1971, 10, 311). The experiments can be carried out using a modified batch method of W. J. Thompson and M. M. Appleman (Biochem. 1979, 18 5228).

The carboline derivatives described in U.S. Pat. No. 6,043,252 are cGMP-specific PDE (PDE V) inhibitors and are suitable for the treatment of a multiplicity of diseases.

The compounds according to the invention are therefore suitable for the treatment of diseases of the cardiovascular system, in particular cardiac insufficiency, and for the treatment and/or therapy of potency disorders (erectile dysfunction).

The compounds according to the invention are furthermore suitable for the treatment of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, furthermore for the treatment of malign hypertonia, phaeochromacytoma (catecholamine-producing tumour of the adrenal cortex), in peripheral vascular (occlusion) diseases, vascular diseases, thrombocytopenia, ulcus pepticum (benign intestinal ulcer), peristaltic motion disorders, percutaneous transluminal coronary angioplasty, carotid angioplasty, postoperative stenosis of the coronary bypass, premonitory pains and benign prostate hyperplasia.

The use of substituted pyrazolopyrimidinones for the treatment of impotence is described, for example, in WO 94/28902.

The compounds are effective as inhibitors of phenylephrine-induced contractions in corpus cavernosum preparations of rabbits.

This biological action can be demonstrated, for example, by the method described by F. Holmquist et al. in J. Urol., 150, 1310-1315 (1993). The inhibition of the contraction demonstrates the effectiveness of the compounds according to the invention for the therapy and/or treatment of potency disorders.

Pharmaceutical formulations consisting of other phosphodiesterase V (PDE V) inhibitors together with a second active ingredient are described in WO 00/15639.

Other combinations are disclosed in WO 00/15228.

Pharmaceutical formulations consisting of other phosphodiesterase V (PDE V) inhibitors together with a prostaglandin or prostaglandin derivative are described in WO 00/15639 and WO 00/15228.

The use of (other) phosphodiesterase IV or V inhibitors in combination with a prostaglandin or prostaglandin derivative for the local treatment of erectile dysfunction is described in WO 99/21558.

R. T. Schermuly et al. in the *American Journal of Respiratory and Critical Care Medicine*, 160, 1500-6 (1999), describe the therapeutic potential of prostaglandin $I_2$ ($PGI_2$) in aerosol form with systemic PDE inhibitors, preferably dual-selective PDE III/IV inhibitors, in low doses for acute and chronic pulmonary hypertension.

In *Pneumologie* (54, Suppl. 1, S42, 2000), R. Schermuly et al. describe the influence of PDE-V inhibition on prostacyclin-induced vasorelaxation in experimental pulmonary hypertonia.

Pharmaceutical formulations consisting of other phosphodiesterase V (PDE V) inhibitors together with calcium antagonists (=calcium channel blockers) are described in WO 00/15639.

Combinations of PDE V inhibitors with endothelin receptor antagonists are described, for example, in WO 99/64004.

Pharmaceutical formulations consisting of other phosphodiesterase V (PDE V) inhibitors together with a nitrate are described in WO 00/15228. The known contraindication of administration of nitrates at the same time as taking of PDE V inhibitors in the indication of erectile dysfunction is described, for example, in WO 00/10542. At the same time, however, it is disclosed that nitrates can be administered as antianginal agents although phosphodiesterase V inhibitors are used at the same time for treatment of erectile dysfunction.

Also described therein are pharmaceutical preparations which comprise both a nitrate and a phosphodiesterase inhibitor for use in the therapy of erectile dysfunction and/or in the therapy of cardiovascular diseases at the same time as the presence of the respective other indication.

The compounds of the formula I can be employed as medicament active ingredients in human and veterinary medicine. They can furthermore be employed as intermediates for the preparation of further medicament active ingredients.

The invention accordingly relates to the compounds of the formula I and to a process for the preparation of compounds of the formula I according to Claim 1 and salts thereof, characterised in that a) a compound of the formula II

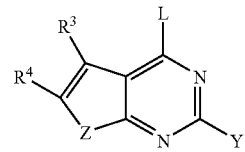

in which

Y, Z, $R^1$ and $R^2$ are as defined in Claim 1, and L is Cl, Br, OH, $SCH_3$ or a reactive esterified OH group, is reacted with a compound of the formula III

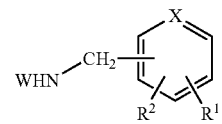

in which

X, W, $R^1$ and $R^2$ are as defined in Claim 1, or b) a radical X in a compound of the formula I is converted into another radical X by, for example, hydrolysing an ester group to a COOH group or converting a COOH group into an amide or into a cyano group, and/or in that a compound of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds according to the invention and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Above and below, the radicals and parameters $R^1$, $R^2$, $R^3$, $R^4$, W, X, Y, Z and L are as defined for the formulae I, II and III, unless expressly stated otherwise.

A is alkyl having 1-6 carbon atoms.

In the above formulae, alkyl is preferably unbranched and has 1, 2, 3, 4, 5 or 6 carbon atoms and is preferably methyl, ethyl or propyl, furthermore preferably isopropyl, butyl, isobutyl, sec-butyl or tert-butyl, but also n-pentyl, neopentyl, isopentyl or hexyl.

A is furthermore alkenyl having 2-6 carbon atoms, for example vinyl or propenyl.

A is furthermore a halogenated alkyl radical, such as, for example, trifluoromethyl.

A' is preferably alkyl having 1, 2, 3, 4, 5 or 6 carbon atoms, —CHAr or —CHAr-A″, where Ar is preferably phenyl.

A″ is preferably alkyl having 1, 2, 3, 4, 5 or 6 carbon atoms.

Hal is preferably F, Cl or Br, but also I.

X is preferably CH, furthermore N.

The radicals $R^1$ and $R^2$ may be identical or different and are preferably located in the 3- or 4-position of the phenyl ring. They are, for example, in each case independently of one another, H, OH, alkyl, F, Cl, Br or I or together are ethyleneoxy, methylenedioxy or ethylenedioxy. They are preferably also in each case alkoxy, such as, for example, methoxy, ethoxy or propoxy.

$R^1$ is, in particular, 3-H, 3-Cl or 3-methoxy.

$R^2$ is, in particular, 4-H, 4-chloro or 4-methoxy.

$R^1$ and $R^2$ together are, in particular, —OCH$_2$O—.

The heterocyclic ring in $R^7$ is preferably 2- or 3-furyl, 2- or 3-thienyl, 1-, 2- or 3-pyrrolyl, 1-, 2-, 4- or 5-imidazolyl, 2-methyl-1-imidazol-1-yl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl.

$R^3$ und $R^4$ together are preferably —(CH$_2$)$_3$—, —(CH$_2$)$_4$— or —CH=CH—CH=CH—.

$R^5$ is a linear or branched alkyl radical having 1-10 carbon atoms, where the alkyl radical is preferably, for example, methyl, ethyl, propyl, isopropyl, butyl, isobutyl, sec-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl.

$R^5$ is furthermore, for example, but-2-enyl or hex-3-enyl.

Very particular preference is given to methyl, ethyl, propyl or butyl, in which one CH$_2$ group is preferably replaced by O.

$R^6$ is cycloalkylalkylene having 5-12 carbon atoms, preferably, for example, cyclopentylmethylene, cyclohexylmethylene, cyclohexylethylene, cyclohexylpropylene or cyclohexylbutylene.

$R^6$ is alternatively cycloalkyl preferably having 5-7 carbon atoms. Cycloalkyl is, for example, cyclopentyl, cyclohexyl or cycloheptyl.

$R^7$ is, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. $R^7$ can thus, for example, also be 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or 8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

$R^7$ is very particularly preferably piperidyl, pyrrolidinyl or piperazinyl.

$R^{10}$, $R^{11}$, $R^{12}$, $R^{13}$ are very particularly preferably H.

Ar is, for example, unsubstituted phenyl, naphthyl or biphenyl, furthermore preferably phenyl, naphthyl or biphenyl which is, for example, monosubstituted, disubstituted or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl or aminocarbonyl.

Ar is very particularly preferably phenyl.

Throughout the invention, all radicals which occur more than once may be identical or different, i.e. are independent of one another.

Accordingly, the invention relates in particular to the compounds of the formula I in which at least one of the said radicals has one of the preferred meanings indicated above. Some preferred groups of compounds may be expressed by the following sub-formulae Ia to In, which conform to the formula I and in which the radicals not designated in greater detail are as defined under the formula I but in which in Ia X is CH;

in Ib $R^9$ is a phenyl radical which is unsubstituted or monosubstituted or disubstituted by COOH, COOA, $CONH_2$, $CONA_2$, CONHA, CN, $NHSO_2A$, $N(SO_2A)_2$ or $SO_2A$;

in Ic Y is phenyl, 1-piperidinyl, piperazinyl or cyclohexyl, each of which is monosubstituted or disubstituted by COOH, COOA or —$S(O)_mA$;

in Id $R^3$ and $R^4$ are each, independently of one another, H, A, OA or Hal,
$R^1$ and $R^2$ together are —O—$CH_2$—$CH_2$—, —O—$CH_2$—O— or —O—$CH_2$—$CH_2$—O,
Y is phenyl, 1-piperidinyl, piperazinyl or cyclohexyl, each of which is monosubstituted or disubstituted by COOH, COOA or —$S(O)_mA$;

in Ie $R^3$ and $R^4$ together are —$(CH_2)_3$—, —$(CH_2)_4$— or —CH=CH—CH=CH—,
$R^1$ and $R^2$ are each, independently of one another, H, OA or Hal,
$R^1$ and $R^2$ together are alternatively alkylene containing —$CH_2$—O—$CH_2$—,
Y is phenyl, 1-piperidinyl, piperazinyl or cyclohexyl, each of which is monosubstituted or disubstituted by COOH, COOA or —$S(O)_mA$;

in If Y is cyclopentylmethylene, cyclohexylmethylene, cyclohexylethylene, cyclohexylpropylene or cyclohexylbutylene, each of which is monosubstituted by COOH or COOA;

in Ig Y is $R^5$ or $R^6$, each of which is substituted by COOH, COOA, $CONH_2$, $CONA_2$, CONHA or —$S(O)_mA$;

in Ih Y is $R^5$, $R^6$ or $R^9$, each of which is substituted by —$(CH_2)_n$—$R^{20}$,
$R^5$ is methyl, ethyl, propyl or butyl,
$R^9$ is phenyl or benzyl,
n is 0 or 1,
$R^{20}$ is COOH, COOA, $CONH_2$, $CONA_2$, CONHA or —$S(O)_mA$;

in Ii X is CH,
Y is $R^5$, $R^6$ or $R^9$, each of which is substituted by —$(CH_2)_n$—$R^{20}$,
$R^5$ is methyl, ethyl, propyl or butyl,
$R^9$ is phenyl or benzyl,
n is 0 or 1,
$R^{20}$ is COOH or COOA;

in Ij X is CH,
Y is $R^5$, $R^6$ or $R^9$, each of which is substituted by —$(CH_2)_n$—$R^{20}$,
Z is NH or NHA',
$R^5$ is methyl, ethyl, propyl or butyl,
$R^9$ is phenyl or benzyl,
n is 0 or 1,
$R^{20}$ is COOH or COOA;

in Ik X is CH,
Y is $R^5$, $R^6$ or $R^9$, each of which is substituted by —$(CH_2)_n$—$R^{20}$,
Z is O,
$R^5$ is methyl, ethyl, propyl or butyl,
$R^9$ is phenyl or benzyl,
n is 0 or 1,
$R^{20}$ is COOH or COOA;

in Il X is CH,
Y is $R^5$, $R^6$ or $R^9$, each of which is substituted by —$(CH_2)_n$—$R^{20}$,
Z is NH or NHA',
$R^3$ and $R^4$ together are alkylene having 3-4 carbon atoms,
$R^5$ is methyl, ethyl, propyl or butyl,
$R^9$ is phenyl or benzyl,
n is 0 or 1,
$R^{20}$ is COOH or COOA;

in Im X is CH,
Y is $R^5$, $R^6$ or $R^9$, each of which is substituted by —$(CH_2)_n$—$R^{20}$,
Z is O,
$R^3$ and $R^4$ together are alkylene having 3-4 carbon atoms,
$R^5$ is methyl, ethyl, propyl or butyl,
$R^9$ is phenyl or benzyl,
n is 0 or 1,
$R^{20}$ is COOH or COOA;

in In $R^1$ and $R^2$ are each, independently of one another, H, A, OH, OA or Hal,
$R^1$ and $R^2$ together are alternatively alkylene having 3-5 carbon atoms, —O—$CH_2$—$CH_2$—, —$CH_2$—O—$CH_2$—, —O—$CH_2$—O— or —O—$CH_2$—$CH_2$—O—,
$R^3$ and $R^4$ are each, independently of one another, H, A or Hal,
$R^3$ and $R^4$ together are alternatively alkylene or alkylidene having 3-5 carbon atoms, or

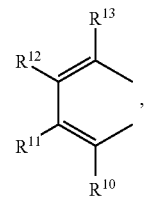

W is H,
X is CH or N,
Y is $(CH_2)_q$—$R^7$, or $R^5$, $R^6$ or $R^9$, each of which is unsubstituted or monosubstituted by $(CH_2)_nR^{20}$,
Z is O, NH or NA',
A' is alkyl having 1-6 carbon atoms, —CHAr or —CHAr-A",
A" is alkyl having 1-6 carbon atoms,
$R^5$ is linear or branched alkyl having 1-10 carbon atoms,
$R^6$ is cycloalkyl or cycloalkylalkylene having 5-12 carbon atoms,
$R^7$ is a saturated or unsaturated, 5-7-membered heterocyclic radical having 1-2 N atoms which is unsubstituted or monosubstituted by $R^{20}$, A, Hal or $CF_3$,
$R^9$ is Ar or $(CH_2)_k$—Ar,
$R^{10}$, $R^{11}$,
$R^{12}$ and $R^{13}$ are H,
$R^{20}$ is —COOH, —COOA or —$S(O)_mA$,
A is alkyl having from 1 to 6 carbon atoms, in which 1-7 H atoms may be replaced by F,
Ar is phenyl,
Hal is F, Cl, Br or I,
k and q are each, independently of one another, 0, 1, 2, 3 or 4,
m is 1 or 2 and
n is 0, 1, 2 or 3;

and physiologically acceptable salts and/or solvates thereof.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

In the compounds of the formula II or III, $R^1$, $R^2$ and X have the meanings indicated, in particular the preferred meanings indicated.

If L is a reactive esterified OH group, this is preferably alkylsulfonyloxy having 1-6 carbon atoms (preferably methylsulfonyloxy) or arylsulfonyloxy having 6-10 carbon atoms (preferably phenyl- or p-tolylsulfonyloxy, furthermore also 2-naphthalenesulfonyloxy).

The compounds of the formula I can preferably be obtained by reacting compounds of the formula II with compounds of the formula III.

If desired, the starting materials can also be formed in situ by not isolating them from the reaction mixture, but instead immediately converting them further into the compounds of the formula I.

On the other hand, it is possible to carry out the reaction stepwise.

The starting compounds of the formulae II and III are generally known. If they are not known, they can be prepared by methods known per se.

The compounds of the formula II are generally prepared from the corresponding 2-aminoindole or 2-aminofuran derivatives.

Compounds of the formula II

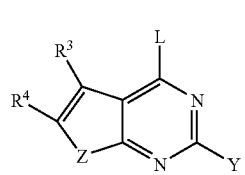

in which
Z is NH or NHA',
L is Cl,
Y is $R^5$, $R^6$ or $R^9$, each of which is unsubstituted or monosubstituted by $(CH_2)_n R^{20}$,
$R^3$ and $R^4$ are each, independently of one another, H, A or Hal,
$R^3$ and $R^4$ together are alternatively alkylene or alkylidene having 3-5 carbon atoms,
and n, $R^{20}$, $R^5$, $R^6$ and $R^9$ are as defined in Claim 1,
are prepared, for example, analogously to the following scheme 1

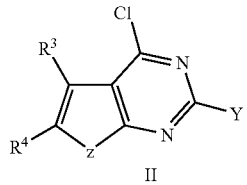

In all formulae of scheme 1,
$R^3$ and $R^4$ are each, independently of one another, H, A or Hal,
$R^3$ and $R^4$ together are alternatively alkylene or alkylidene having 3-5 carbon atoms.

In the compounds of the formula IIa, Z is NH or NA', where A' is as defined in Claim 1.

In the compounds of the formula IIb,
A and A' are each, independently of one another, H or alkyl having 1, 2, 3 or 4 carbon atoms, and
Y is $R^5$, $R^6$ or $R^9$, each of which is unsubstituted or monosubstituted by $(CH_2)_n R^{20}$,
and where n, $R^{20}$, $R^5$, $R^6$ and $R^9$ are as defined in Claim 1.

In the compounds of the formula IIc, Z is NH or NA', where A' is as defined in Claim 1.

Compounds of the formula II

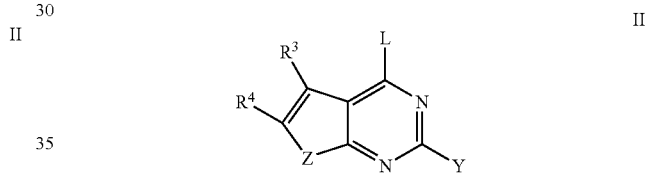

in which
Z is O,
L is Cl,
Y is $R^5$, $R^6$ or $R^9$, each of which is unsubstituted or monosubstituted by $(CH_2)_n R^{20}$,
$R^3$ and $R^4$ are each, independently of one another, H, A or Hal,
$R^3$ and $R^4$ together are alternatively alkylene or alkylidene having 3-5 carbon atoms,
and n, $R^{20}$, $R^5$, $R^6$ and $R^9$ are as defined in Claim 1,
are prepared, for example, analogously to the following scheme 2

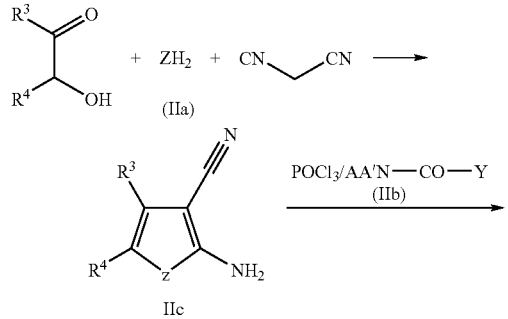

Scheme 1

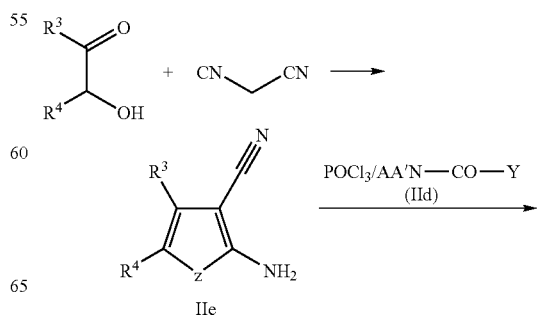

Scheme 2

-continued

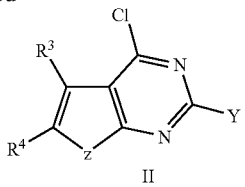

In all formulae of scheme 2, $R^3$ and $R^4$ are each, independently of one another, H, A or Hal, $R^3$ and $R^4$ together are alternatively alkylene or alkylidene having 3-5 carbon atoms.

In the compounds of the formula IId,

A and A' are each, independently of one another, H or alkyl having 1, 2, 3 or 4 carbon atoms, and Y is $R^5$, $R^6$ or $R^9$, each of which is unsubstituted or monosubstituted by $(CH_2)_n R^{20}$, and where n, $R^{20}$, $R^5$, $R^6$ and $R^9$ are as defined in Claim 1.

In the compounds of the formula IIe, Z is O (oxygen).

Compounds of the formula II

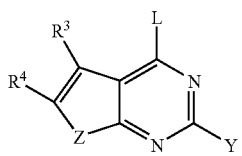

in which

Z is O,

L is Cl,

Y is $(CH_2)_q$—$R^7$, $R^3$ and $R^4$ are each, independently of one another, H, A or Hal, $R^3$ and $R^4$ together are alternatively alkylene or alkylidene having 3-5 carbon atoms, q and $R^7$ are as defined in Claim 1, and where $R^7$ contains at least one N atom, are prepared, for example, analogously to the following scheme 3

Scheme 3

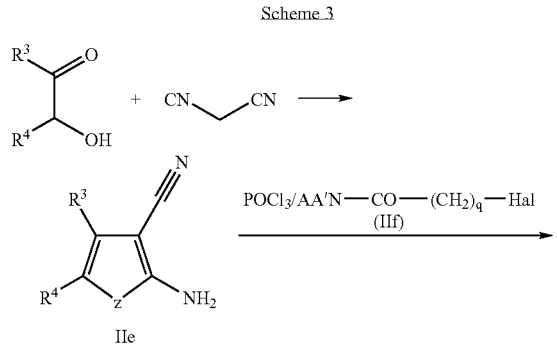

-continued

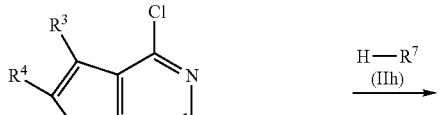

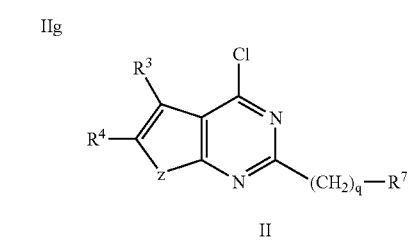

In all formulae of scheme 3, $R^3$ and $R^4$ are each, independently of one another, H, A or Hal, $R^3$ and $R^4$ together are alternatively alkylene or alkylidene having 3-5 carbon atoms.

In the compounds of the formula IIf,

A and A' are each, independently of one another, H or alkyl having 1, 2, 3 or 4 carbon atoms, and Hal is Cl or Br.

In the compounds of the formula IIg,

Z is O, q is 0,1,2,3 or 4,

Hal is Br or Cl.

In the compounds of the formula IIh, $R^7$ is as defined in Claim 1, where the heterocyclic radical contains at least one substitutable nitrogen.

Compounds of the formula II

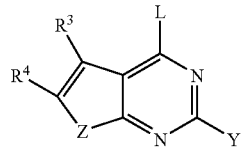

in which

Z is NH,

L is Cl,

Y is $R^5$, $R^6$ or $R^9$, each of which is unsubstituted or monosubstituted by $(CH_2)_n R^{20}$, $R^3$ and $R^4$ together are

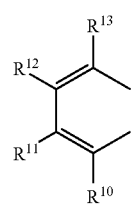

n, $R^{20}$, $R^5$, $R^6$ and $R^9$ are as defined in Claim 1, are prepared, for example, analogously to the following scheme 4

Scheme 4

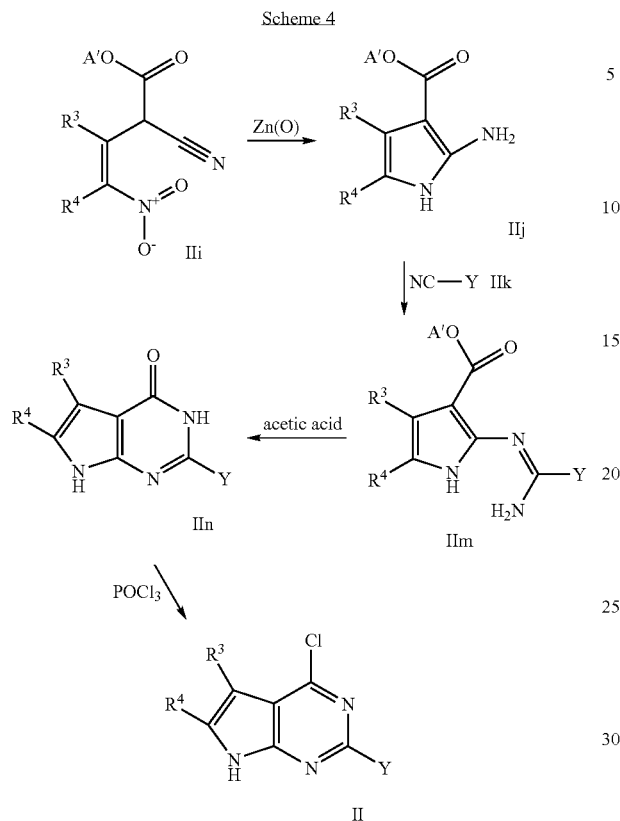

In all formulae of scheme 4,
$R^3$ and $R^4$ together are

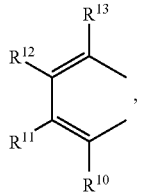

where $R^{10}$, $R^{11}$, $R^{12}$ and $R^{13}$ are as defined in Claim 1.

The compounds of the formula IIi are prepared, for example, analogously to I. T. Fordes, C. N. Johnson, M. Thompson, J. Chem. Soc. Perkin Trans. 1, 2, 275-282 (1992).

In the compounds of the formula IIi, A' is alkyl having 1, 2, 3 or 4 carbon atoms.

In the compounds of the formula IIj, A' is alkyl having 1, 2, 3 or 4 carbon atoms.

In the compounds of the formula IIk, Y is $R^5$, $R^6$ or $R^9$, each of which is unsubstituted or monosubstituted by $(CH_2)_n R^{20}$, where n, $R^{20}$, $R^5$, $R^6$ and $R^9$ are as defined in Claim 1.

In the compounds of the formula IIm, A' is alkyl having 1, 2, 3 or 4 carbon atoms, and Y is $R^5$, $R^6$ or $R^9$, each of which is unsubstituted or monosubstituted by $(CH_2)_n R^{20}$, where n, $R^{20}$, $R^5$, $R^6$ and $R^9$ are as defined in Claim 1.

In the compounds of the formula IIn, Y is $R^5$, $R^6$ or $R^9$, each of which is unsubstituted or monosubstituted by $(CH_2)_n R^{20}$, where n, $R^{20}$, $R^5$, $R^6$ and $R^9$ are as defined in Claim 1.

Compounds of the formula II

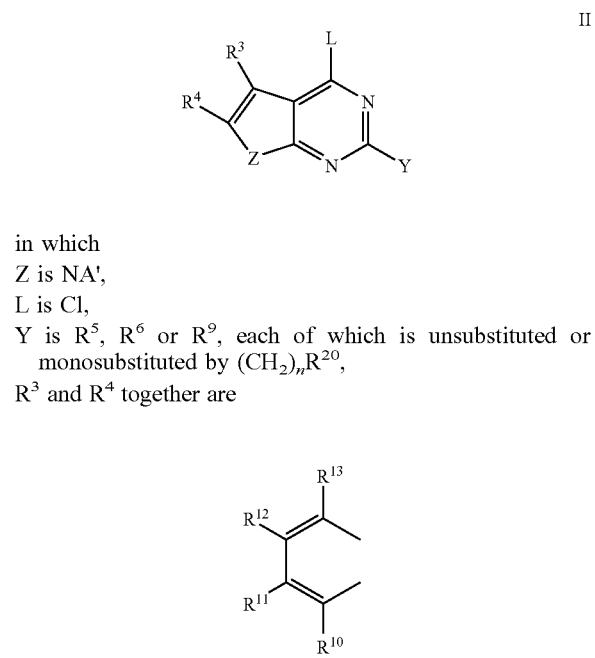

in which
Z is NA',
L is Cl,
Y is $R^5$, $R^6$ or $R^9$, each of which is unsubstituted or monosubstituted by $(CH_2)_n R^{20}$,
$R^3$ and $R^4$ together are are prepared, for example, analogously to the following scheme 5

A', n, $R^{20}$, $R^5$, $R^6$ and $R^9$ are as defined in Claim 1,

Scheme 5

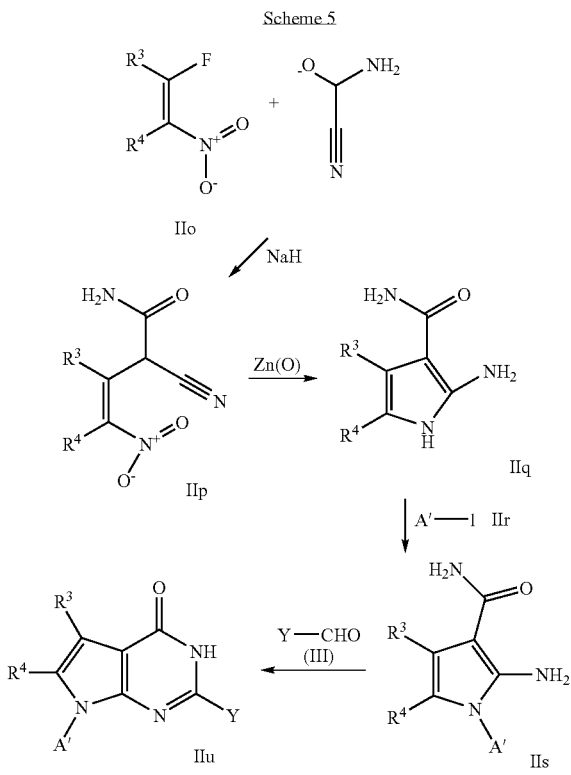

-continued

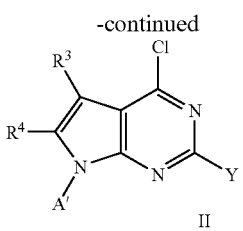

In all formulae of scheme 5,
$R^3$ and $R^4$ together are

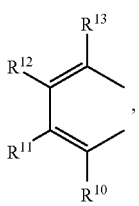

where $R^{10}$, $R^{11}$, $R^{12}$ and $R^{13}$ are as defined in Claim 1.

In the compounds of the formulae IIs and IIu, A' is as defined in Claim 1. In compound IIt, Y is $R^5$, $R^6$ or $R^9$, each of which is unsubstituted or monosubstituted by $(CH_2)_n R^{20}$, where n, $R^{20}$, $R^5$, $R^6$ and $R^9$ are as defined in Claim 1.

In detail, the reaction of the compounds of the formula II with the compounds of the formula III is carried out in the presence or absence of an inert solvent at temperatures between about −20 and about 150°, preferably between 20 and 100°.

The addition of an acid-binding agent, for example an alkali or alkaline earth metal hydroxide, carbonate or bicarbonate or another salt of a weak acid of the alkali or alkaline earth metals, preferably of potassium, sodium or calcium, or the addition of an organic base, such as triethylamine, dimethylamine, pyridine or quinoline or of an excess of the amine component, may be favourable.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

It is furthermore possible to convert a radical X in a compound of the formula I into another radical X, for example by hydrolysing an ester or a cyano group to give a COOH group.

Ester groups can be saponified, for example, using NaOH or KOH in water, water/THF or water/dioxane at temperatures between 0 and 100°. Carboxylic acids can be converted into the corresponding carboxylic acid chlorides, for example using thionyl chloride, and these can be converted into carboxamides. Elimination of water therefrom in a known manner gives carbonitriles.

An acid of the formula I can be converted into the associated acid-addition salt using a base, for example by reaction of equivalent amounts of the acid and the base in an inert solvent, such as ethanol, followed by evaporation. Suitable bases for this reaction are, in particular, those which give physiologically acceptable salts.

Thus, the acid of the formula I can be converted into the corresponding metal salt, in particular alkali metal or alkaline earth metal salt, or into the corresponding ammonium salt using a base (for example sodium hydroxide, potassium hydroxide, sodium carbonate or potassium carbonate). Also suitable for this reaction are, in particular, organic bases which give physiologically acceptable salts, such as, for example, ethanolamine.

On the other hand, a base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable acids. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purification of the compounds of the formula I.

Compounds of the formula I according to the invention may be chiral owing to their molecular structure and may accordingly occur in various enantiomeric forms. They may therefore be in racemic or in optically active form.

Since the pharmaceutical efficacy of the racemates or the stereoisomers of the compounds according to the invention may differ, it may be desirable to use the enantiomers. In these cases, the end product, or, however, even the intermediates may be resolved to give enantiomeric compounds by chemical or physical measures known to the person skilled in the art or employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline) or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical preparation), in particular by non-chemical methods. They can be converted into a suitable dosage form here together with at least one solid, liquid and/or semi-liquid excipient or adjuvant and optionally in combination with one or more further active ingredients.

The invention furthermore relates to medicaments comprising at least one compound of the formula I and physiologically acceptable derivatives, solvates and stereoisomers thereof, including mixtures thereof in all ratios, and, if desired, excipients and adjuvants.

The invention furthermore relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and do no react with the novel compounds, for example water, vegetable oils, benzyl alcohols, alkylene glycols, polyethylene glycols, glycerol triacetate, gelatine, carbohydrates, such as lactose or starch, magnesium stearates, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as a nasal spray. The novel compounds may also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances, colorants and flavours and/or a plurality of further active ingredients, for example one or more vitamins.

The compounds of the formula I and physiologically acceptable salts thereof can be employed for combating diseases in which an increase in the cGMP (cycloguanosine monophosphate) level results in inflammation inhibition or prevention and muscle relaxation. The compounds according to the invention are used in particular in the treatment of diseases of the cardiovascular system and for the treatment and/or therapy of potency disorders in humans.

The invention relates to the use of the compounds of the formula I and physiologically acceptable salts and/or solvates thereof for the preparation of a medicament for the treatment of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, for the treatment of malign hypertonia, phaeochromacytoma, peripheral vascular (occlusion) diseases, vascular diseases, thrombocytopenia, ulcus pepticum, peristaltic motion disorders, percutaneous transluminal coronary angioplasty, carotid angioplasty, postoperative stenosis of the coronary bypass, premonitory pains and benign prostate hyperplasia.

In general, the substances are preferably administered in doses of between about 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or physiologically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or physiologically usable derivatives, solvates and stereoisomers thereof, including mixtures thereof in all ratios, and
(b) an effective amount of a further medicament active ingredient.

The set comprises suitable containers, such as boxes, individual bottles, cartons, bags or ampoules. The set may comprise, for example, separate ampoules each containing an effective amount of a compound of the formula I and/or physiologically usable derivatives, solvates and stereoisomers thereof, including mixtures thereof in all ratios, and an effective amount of a further medicament active ingredient in dissolved or lyophilised form.

The invention furthermore relates to the use of compounds of the formula I and/or physiologically usable derivatives, solvates and stereoisomers thereof, including mixtures thereof in all ratios, for the preparation of a medicament for the treatment of diseases of the cardiovascular system, for the treatment and/or therapy of potency disorders, such as, for example, erectile dysfunction, for the treatment of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, furthermore for the treatment of malign hypertonia, phaeochromacytoma (catecholamine-producing tumour of the pituitary cortex), in peripheral vascular (occlusion) diseases, vascular diseases, thrombocytopenia, ulcus pepticum (benign intestinal ulcer), peristaltic motion disorders, percutaneous transluminal coronary angioplasty, carotid angioplasty, postoperative stenosis of the coronary bypass, premonitory pains and benign prostate hyperplasia, in combination with at least one further medicament active ingredient.

The compounds of the formula I according to the invention can be used together with other active ingredients, such as, for example, with vasodilators, α-adrenergic inhibitors, such as, for example, phentolamin, prazocin or yohimbin, mixed α,β-inhibitors, such as, for example, carvedilol, prostaglandin El and prostacyclin, ACE (angiotensin converting enzyme) inhibitors, NEP (neutral endopeptidase) inhibitors, centrally acting dopaminergic active ingredients, such as, for example, apomorphine, vaso-active intestinal peptides, calcium channel blockers and compounds such as thiazides.

The invention therefore relates to pharmaceutical formulations comprising a prostaglandin or prostaglandin derivative and at least one compound of the formula I.

Preference is given to prostaglandins or prostaglandin derivatives selected from the group consisting of $PGE_0$, $PGA_1$, $PGB_1$, $PGF_{1\alpha}$, $PGA_2$, $PGB_2$, 19-hydroxy-$PGA_1$, 19-hydroxy-$PGB_1$, 19-hydroxy-$PGA_2$, 19-hydroxy-$PGB_2$, $PGE_3$, $PGF_{3\alpha}$, alprostadil ($PGE_1$), dinoprost ($PGF_2$), dinoprostone ($PGE_2$), epoprostenol sodium ($PGI_2$; prostacyclin sodium), gemeprost, iloprost, latanoprost, misoprostol, sulprostone, carboprost thromethamin, dinoprost thromethamin, lipoprost, metenoprost and tiaprost.

Particular preference is given to prostaglandins or prostaglandin derivatives selected from the group consisting of alprostadil ($PGE_1$), dinoprost ($PGF_2$), dinoprostone ($PGE_2$), epoprostenol sodium ($PGI_2$; prostacyclin sodium), gemeprost, iloprost, latanoprost, misoprostol, sulprostone, carboprost thromethamin, dinoprost thromethamin, lipoprost, metenoprost and tiaprost.

Particular preference is given to $PGE_1$ or prostacyclin, especially preferably prostacyclin.

The invention preferably relates to pharmaceutical formulations comprising a calcium antagonist and at least one compound of the formula I.

Preference is given to calcium antagonists selected from the group consisting of selective and non-selective calcium antagonists.

Preference is given to selective calcium antagonists selected from the group consisting of dihydropyridine derivatives, phenylalkylamine derivatives, benzothiazepine derivatives and other selective calcium antagonists.

Dihydropyridine derivatives are preferably selected from the group consisting of amlodipine, felodipine, isradipine, nicardipine, nifedipine, nimodipine, nisoldipine, nitrendipine, lacidipine, nilvadipine, manidipine, barnidipine and lercanidipine.

The phenylalkylamine derivatives are preferably selected from the group consisting of verapamil and gallopamil.

The benzothiazepine derivatives are preferably diltiazem.

The other selective calcium antagonists are preferably mibefradil.

The non-selective calcium antagonists are preferably selected from the group consisting of fendiline, bepridil, lidoflazine and perhexiline.

The invention furthermore relates to pharmaceutical formulations comprising an antithrombotic and at least one compound of the formula I. The term antithrombotics also includes so-called anticoagulants and blood platelet aggregation inhibitors (thrombocyte aggregation inhibitors). Preferred antithrombotics are vitamin K antagonists, heparin compounds, thrombocyte aggregation inhibitors, enzymes, factor Xa inhibitors, factor VIIa inhibitors and other antithrombotic agents.

Preferred vitamin K antagonists are selected from the group consisting of dicoumarol, phenindione, warfarin, phenprocoumon, acenocoumarol, ethyl biscoumacetate, clorindione, diphenadione and tioclomarol.

Preferred heparin compounds are selected from the group consisting of heparin, antithrombin III, dalteparin, enoxaparin, nadroparin, parnaparin, reviparin, danaparoid, tinzaparin and sulodexide.

Preferred thrombocyte aggregation inhibitors are selected from the group consisting of ditazole, cloricromen, picotamide, clopidogrel, ticlopidine, acetylsalicylic acid, dipyridamole, calcium carbassalate, epoprostenol, indobufen, iloprost, abciximab, tirofiban, aloxiprin and intrifiban.

Preferred enzymes are selected from the group consisting of streptokinase, alteplase, anistreplase, urokinase, fibrinolysin, brinase, reteplase and saruplase.

Preferred antithrombotics are furthermore the blood platelet glycoprotein receptor (IIb/IIIa) antagonists which inhibit blood platelet aggregation.

Preferred compounds are described, for example, in EP 0 623615 B1 on page 2 or in EP 0 741 133 A2, page 2, line 2, to page 4, line 56.

Preferred factor Xa and VIIa inhibitors are, for example, the compounds of the formula I described in WO 99/16751, WO 99/31092, WO 99/57096, WO 00/12479, WO 00/20416, WO 00/40583 and WO 00/51989.

Other preferred factor Xa inhibitors are, for example, the compounds described in the following documents:
a) in WO 97/30971, page 4, line 5, to page 13, line 19;
b) in EP 0 921 116 A1, page 2, line 1, to line 51;
c) in EP 0 540 051 B1, page 2, line 41, to page 3, line 14;
d) in EP 0 798 295 A1, page 69, line 10, to page 71, page 53.

Other preferred compounds are selected from the group consisting of defibrotide, desirudin and lepirudin.

The invention also relates to pharmaceutical formulations comprising an endothelin receptor antagonist and at least one compound of the formula I.

Preferred endothelin receptor antagonists are bosentan, tezosentan and sitaxentan (TBC-11251; J. Med. Chem., 40, No. 11, 1690-97, 1997).

Preferred endothelin receptor antagonists are thus furthermore
a) BMS-193884 (EP 558258),
b) BMS-207940 (Pharmaprojects (13 Jun. 1997)),
c) BQ-123 (Exp. Opin. Invest. Drugs, 1997, 6, No. 5, 475-487),
d) SB-209670 (Exp. Opin. Invest. Drugs, 1997, 6, No. 5, 475-487),
e) SB-217242 (Exp. Opin. Invest. Drugs, 1997, 6, No. 5, 475-487),
f) SB-209598 (Trends in Pharmacol. Sci., 17, 177-81, 1996),
g) TAK-044 (Exp. Opin. Invest. Drugs, 1997, 6, No. 5, 475-487),
h) Bosentan (Trends in Pharmacol. Sci., 18, 408-12, 1997),
i) PD-156707 (J. Med. Chem., 40, No. 7, 1063-74, 1997),
j) L-749329 (Bioorg. Med. Chem. Lett., 7, No. 3, 275-280,1997),
k) L-754142 (Exp. Opin. Invest. Drugs, 1997, 6, No. 5, 475-487),
l) ABT-627 (J. Med. Chem., 40, No. 20, 3217-27, 1997),
m) A-127772 (J. Med. Chem., 39, No. 5, 1039-1048, 1996),
n) A-206377 (213th American Chemical Society National Meeting, San Francisco, Calif., USA, 13-17 Apr. 1997, Poster, MEDI 193),
o) A-182086 (J. Med. Chem., 40, No. 20, 3217-27, 1997),
p) EMD-93246 (211th American Chemical Society National Meeting, New Orleans, USA, 1996, Poster, MEDI 143),
q) EMD-122801 (Bioorg. Med. Chem. Lett., 8, No. 1, 17-22, 1998),
r) ZD-1611 (Trends in Pharmacol. Sci., 18, 408-12, 1997),
s) AC-610612 (R&D Focus Drug News (18 May 1998)),
t) T-0201 (70th Annual Meeting of the Japanese Pharmacological Society, Chiba, Japan, 22-15 Mar. 1997, Lecture, O-133),
u) J-104132 (R&D Focus Drug News (15 Dec. 1997)),

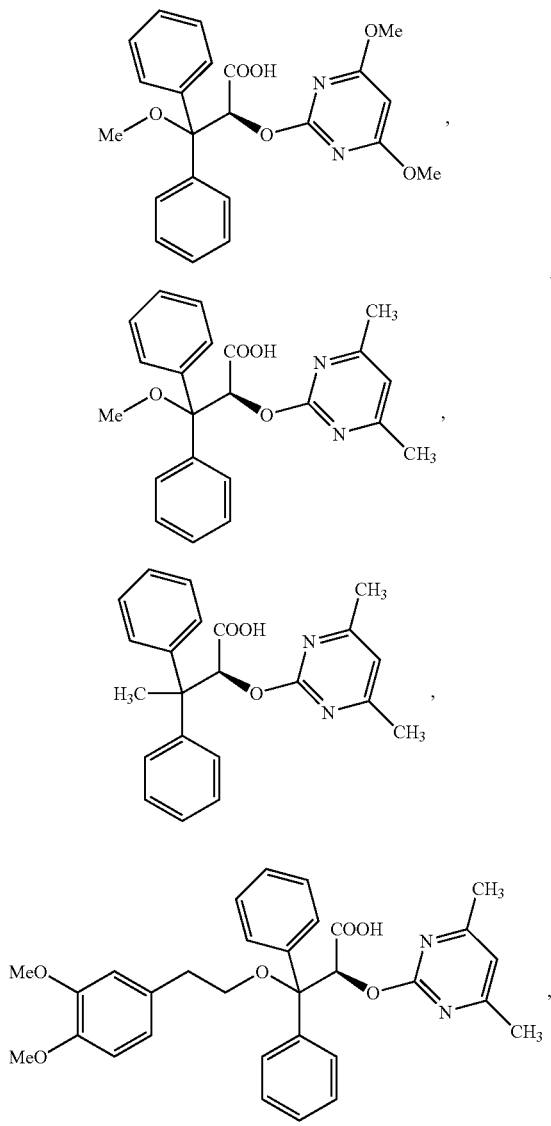

Particularly preferred endothelin receptor antagonists are, for example, the compounds of the formula I described in EP 0733626, EP 0733626, EP 0755934, EP 0757039, EP 0796250, WO 97/19077, WO 97/30982, WO 97/30996, DE 19609597, DE 19612101, WO 98/27091, WO 98/27077, WO 98/41515, WO 98/41521, WO 98/42702, WO 98/42709 or WO 99/05132.

The invention furthermore relates to pharmaceutical formulations comprising a vasodilator, such as, for example, a nitrate, and at least one compound of the formula I.

The invention preferably relates to pharmaceutical formulations comprising at least one compound of the formula I and a vasodilator, such as, for example, (a) an organic nitrate, for example nitroglycerine, isosorbide mononitrate, isosorbide dinitrate, pentaerythrityl tetra-, tri-, di-, tri- or mono-nitrate, propatyl nitrate, trol nitrate, nicroandil, mannitol hexanitrate, inositol hexanitrate, N-[3-nitratopivaloyl]-L-cysteine ethyl ester, (b) an organic nitrite, for example isoamyl nitrite, (c) a thionitrite, (d) a thionitrate, (e) an S-nitrosothiol, such as, for example, S-nitroso-N-acetyl-D,L-penicillamine, (f) nitrosoproteins, (g) substituted furoxanes, such as, for example, 1,2,5-oxadiazole 2-oxides or furazane N-oxides, (h) substituted sydnonimines, such as, for example, molsidomine or mesocarb, (i) complex nitrosyl compounds, such as, for example, iron nitrosyl compounds, preferably sodium nitroprusside, or (j) nitrogen oxide NO, which is inhaled.

Preferred vasodilators are nitrates selected from the group consisting of pentaerythrityl tetra-, tri-, di- and mononitrate, isosorbide mononitrate, isosorbide dinitrate and glycerol trinitrate.

Particular preference is given to nitrates selected from the group consisting of pentaerythrityl tetranitrate, isosorbide mononitrate, isosorbide dinitrate, glycerol trinitrate, very particularly preferably pentaerythrityl tetranitrate.

The invention furthermore relates to the use of a pharmaceutical formulation comprising at least one compound of the formula I and at least one antithrombotic for the preparation of a medicament for the treatment of pulmonary hypertension, congestive heart failure (CHF), chronic obstructive pulmonary disease (COPD), cor pulmonale and/or dextrocardiac insufficiency.

α-adrenergic inhibitors inhibit the vasoconstriction in the corpus cavernosum. Since PDE V inhibitors increase vasodilation of the same tissue of the smooth muscles, potency disorders (erectile dysfunction) can preferably also be treated using pharmaceutical formulations comprising at least one compound of the formula I and at least one α-adrenergic inhibitor, such as, for example, phentolamin or prazocin, or at least one centrally acting dopaminergic active ingredient, such as, for example, apomorphine.

The invention therefore furthermore relates to the use of a pharmaceutical formulation comprising at least one compound of the formula I and at least one α-adrenergic inhibitor, such as, for example, phentolamin or prazocin, or at least one centrally acting dopaminergic active ingredient, such as, for example, apomorphine, for the preparation of a medicament for the treatment of potency disorders.

The invention furthermore relates to the use of a pharmaceutical formulation comprising at least one compound of the formula I and a calcium antagonist for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one nitrate for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one endothelin receptor antagonist for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one prostaglandin or a prostaglandin derivative for the preparation of a medicament for the treatment of pulmonary hypertension, congestive heart failure (CHF), chronic obstructive pulmonary disease (COPD), cor pulmonale and/or dextrocardiac insufficiency.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS): EI (electron impact ionisation) $M^+$ FAB (fast atom bombardment) $(M+H)^+$

EXAMPLE 1

Preparation of 4-[4-(3-chloro-4-methoxybenzylamino)-9-(1-phenylethyl)-6,7,8,9-tetrahydro-5H-1,3,9-triazafluoren-2-yl]benzoic acid 1.1 A solution of 56.6 g of 2-hydroxycyclohexanone, 60.6 g of phenethylamine and a catalytic amount of p-toluenesulfonic acid in 400 ml of cyclohexanone is refluxed for 10 hours on a water separator. The solution is cooled to 50°, 10 ml of piperidine and 30 ml of malononitrile, dissolved in hot cyclohexanone, are then added, and the mixture is refluxed for a few hours more.

Removal of the solvent and conventional work-up give 45 g of 2-amino-1-(1-phenylethyl)-4,5,6,7-tetrahydro-1H-indole-3-carbonitrile ("AA"), m.p. 129°,

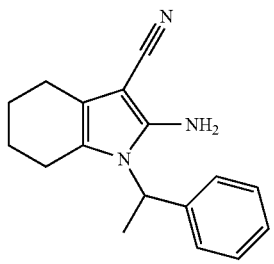

"AA"

1.2 1 ml of $POCl_3$ is added with ice cooling to 1.8 g of methyl 4-N,N-dimethylaminocarbonylbenzoate, and the mixture is stirred for about a further 30 minutes. 2 g of "AA" are added, and the mixture is stirred at 80° for 3 hours, then subjected to conventional work-up, giving 1.6 g of methyl 4-[4-chloro-9-(1-phenylethyl)-6,7,8,9-tetrahydro-5H-1,3,9-triazafluoren-2-yl]benzoate ("AB"),

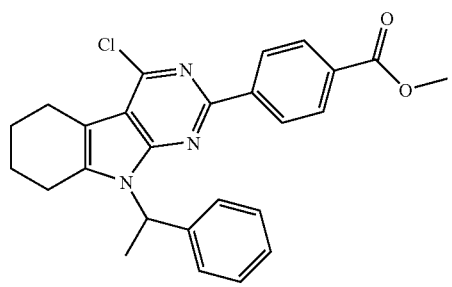

"AB"

1.3 3-chloro-4-methoxybenzylamine is added to a solution of 1.6 g of "AB" in 30 ml of 1-methyl-2-pyrrolidone, and the mixture is stirred at 100° for 4 hours. Conventional work-up gives 1.4 g of methyl 4-[4-(3-chloro-4-methoxybenzylamino)-9-(1-phenylethyl)-6,7,8,9-tetrahydro-5H-1,3,9-triazafluoren-2-yl]benzoate ("AC").

1.4 20 ml of NaOH are added to 0.5 g of "AC" in 20 ml of ethylene glycol monoethyl ether, and the mixture is heated on a steam bath for 3 hours. The ether is removed, and the residue is diluted with water and washed with ethyl acetate. The ethyl acetate is discarded. The mixture is acidified using glacial acetic acid, and the crystals which deposit are separated off. The residue is dissolved in methanol, and methanolic KOH is added. The methanol is removed under reduced pressure. Water is added to the residue, and the crystals which deposit are filtered off with suction, giving 0.11 g of 4-[4-(3-chloro-4-methoxybenzylamino)-9-(1-phenylethyl)-6,7,8,9-tetrahydro-5H-1,3,9-triazafluoren-2-yl]benzoic acid, potassium salt, m.p. 179°.

Affinity to PDE V: $IC_{50}$ [mol/l]3.0E-07

Analogous reaction of methyl 4-[4-chloro-6,7,8,9-tetrahydro-5H-1,3,9-triazafluoren-2-yl]benzoate with benzylamine, 3,4-dimethoxybenzylamine, 3,4-dichlorobenzylamine, 3,4-methylenedioxybenzylamine followed by ester hydrolysis gives 4-[4-benzylamino-9-(1-phenylethyl)-6,7,8,9-tetrahydro-5H-1,3,9-triazafluoren-2-yl]benzoic acid;

4-[4-(3,4-dimethoxybenzylamino)-9-(1-phenylethyl)-6,7,8,9-tetrahydro-5H-1,3,9-triazafluoren-2-yl]benzoic acid;

4-[4-(3,4-dichlorobenzylamino)-9-(1-phenylethyl)-6,7,8,9-tetrahydro-5H-1,3,9-triazafluoren-2-yl]benzoic acid;

4-[4-(3,4-methylenedioxybenzylamino)-9-(1-phenylethyl)-6,7,8,9-tetrahydro-5H-1,3,9-triazafluoren-2-yl]benzoic acid.

Analogous reaction of methyl 4-[4-chloro-6,7,8,9-tetrahydro-5H-1,3,9-triazafluoren-2-yl]-butyrate with 3-chloro-4-methoxybenzylamine, benzylamine, 3,4-dimethoxybenzylamine, 3,4-dichlorobenzylamine, 3,4-methylenedioxybenzylamine followed by ester hydrolysis gives 4-[4-(3-chloro-4-methoxybenzylamino)-9-(1-phenylethyl)-6,7,8,9-tetrahydro-5H-1,3,9-triazafluoren-2-yl]butyric acid, ethanolamine salt;

4-[4-benzylamino-9-(1-phenylethyl)-6,7,8,9-tetrahydro-5H-1,3,9-triazafluoren-2-yl]butyric acid;

4-[4-(3,4-dimethoxybenzylamino)-9-(1-phenylethyl)-6,7,8,9-tetrahydro-5H-1,3,9-triazafluoren-2-yl]butyric acid;

4-[4-(3,4-dichlorobenzylamino)-9-(1-phenylethyl)-6,7,8,9-tetrahydro-5H-1,3,9-triazafluoren-2-yl]butyric acid;

4-[4-(3,4-methylenedioxybenzylamino)-9-(1-phenylethyl)-6,7,8,9-tetrahydro-5H-1,3,9-triazafluoren-2-yl]butyric acid.

EXAMPLE 2

Preparation of 4-[4-(3,4-methylenedioxybenzy-lamino)-5,6,7,8-tetrahydrobenzo[4,5]furo[2,3-d]pyrimidin-2-yl]benzoic acid

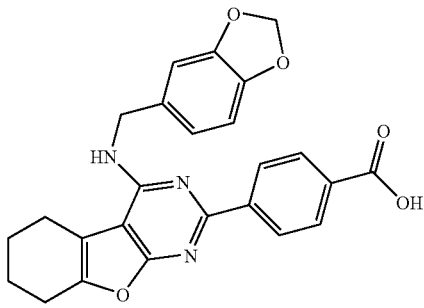

2.1 4.8 ml of triethylamine are added dropwise to a solution of 11.0 g of 2-hydroxycyclohexanone and 9.6 g of malononitrile in 25 ml of methanol, and the mixture is stirred at room temperature for a further 4 hours. The crystals which deposit are separated off and washed with methanol, giving 12.8 g of 2-amino-4,5,6,7-tetrahydrobenzofuran-3-carbonitrile ("BA"), m.p. 179°.

2.2 30 ml of a 40% dimethylamine solution in 200 ml of THF are initially introduced. 20 g of methyl 4-chlorocarbonylbenzoate are dissolved in 300 ml of THF and added dropwise, and the mixture is stirred at room temperature for a further 2 hours. The solvent is removed, and the mixture is subjected to conventional work-up, giving 19.2 g of methyl 4-(N,N-dimethylaminocarbonyl)benzoate ("BB"), m.p. 107°.

2.3 3.3 ml of POCl$_3$ are added to 5.0 g of "BB" with ice cooling, and the mixture is stirred for about a further 30 minutes. 5.9 g of "BA" are then added, and the mixture is stirred at 80° for 3 hours.

Conventional work-up gives 5.2 g of methyl 4-(4-chloro-5,6,7,8-tetrahydrobenzo[4,5]furo[2,3-d]pyrimidin-2-yl)benzoate ("BC"), amorphous.

2.4 2.4 g of 3,4-methylenedioxybenzylamine are added to a solution of 2.5 g of "BC" in 30 ml of 1-methyl-2-pyrrolidone, and the mixture is stirred at 100° for 4 hours. The mixture is subjected to conventional work-up, giving 2.2 g of methyl 4-[4-(3,4-methylenedioxybenzylamino)-5,6,7,8-tetrahydrobenzo[4,5]furo[2,3-d]pyrimidin-2-yl]benzoate ("BD").

2.5 10 ml of NaOH are added to 1.0 g of "BD" in 10 ml of ethylene glycol monoethyl ether, and the mixture is heated on a steam bath for 3 hours. The ether is removed, and the residue is diluted with water and washed with ethyl acetate. The ethyl acetate is discarded. The mixture is acidified using glacial acetic acid, and the crystals which deposit are separated off. The residue is dissolved in isopropanol, and ethanolamine is added. Salt is etherified out, giving 0.5 g of 4-[4-(3,4-methylenedioxybenzylamino)-5,6,7,8-tetrahydrobenzo[4,5]furo[2,3-d]pyrimidin-2-yl]benzoic acid, ethanolamine salt, m.p. 205°.

Analogous reaction of
methyl 4-(4-chloro-5,6,7,8-tetrahydrobenzo[4,5]furo[2,3-d]pyrimidin-2-yl)benzoate with
3-chloro-4-methoxybenzylamine,
benzylamine,
3,4-dimethoxybenzylamine,
3,4-dichlorobenzylamine,
C-pyridin-3-ylmethylamine followed by ester hydrolysis gives 4-[4-(3-chloro-4-methoxybenzylamino)-5,6,7,8-tetrahydrobenzo[4,5]furo[2,3-d]pyrimidin-2-yl]benzoic acid, ethanolamine salt, m.p. 205°;

4-(4-benzylamino-5,6,7,8-tetrahydrobenzo[4,5]furo[2,3-d]pyrimidin-2-yl)benzoic acid, ethanolamiine salt;

4-[4-(3,4-dimethoxybenzylamino)-5,6,7,8-tetrahyd robenzo[4,5]furo[2,3-d]pyrimidin-2-yl]benzoic acid, ethanolamine salt;

4-[4-(3,4-dichlorobenzylamino)-5,6,7,8-tetrahydrobenzo[4,5]furo[2,3-d]pyrimidin-2-yl]benzoic acid, ethanolamine salt;

4-{4-[(pyridin-3-ylmethyl)amino]-5,6,7,8-tetrahydrobenzo[4,5]furo[2,3-d]pyrimidin-2-ylbenzoic acid, ethanolamine salt, m.p.>250°.

EXAMPLE 3

Preparation of Preparation of 4-[4-(3-chloro-4-methoxybenzylamino)-5,6,7,8-tetrahydrobenzo[4,5]furo[2,3-d]pyrimidin-2-yl]benzoic acid 3.1 3.3 ml of POCl$_3$ are added with ice cooling to 5.5 g of methyl 4-(N,N-dimethylcarbamoyl)butyrate, and the mixture is stirred for about a further 30 minutes. 5.9 g of "BA" are then added, and the mixture is stirred at 80° for 3 hours.

Conventional work-up gives 5.2 g of methyl 4-(4-chloro-5,6,7,8-tetrahydrobenzo[4,5]furo[2,3-d]pyrimidin-2-yl)butyrate ("CA"), amorphous.

3.2 2.3 g of 3-chloro-4-methoxybenzylamine are added to a solution of 2.0 g of "CA" in 20 ml of 1-methyl-2-pyrrolidone, and the mixture is stirred at 80° for 3 hours. The mixture is subjected to conventional work-up, giving 2.2 g of methyl 4-[4-(3-chloro-4-methoxybenzylamino)-5,6,7,8-tetrahydrobenzo[4,5]furo[2,3-d]pyrimidin-2-yl]butyrate ("CB").

3.3 10 ml of 2N NaOH are added to 0.8 g of "CB" in 10 ml of methanol, and the mixture is stirred at 50° for a further 2 hours. The alcohol is removed, and the residue is diluted with water and washed with ethyl acetate. The ethyl acetate is discarded. The mixture is acidified using HCl and subjected to conventional work-up. The residue is dissolved in ethanol, and cyclohexylamine is added. The crystals which deposit are washed with ether, giving 0.25 g of 4-[4-(3-chloro-4-methoxybenzylamino)-5,6,7,8-tetrahydrobenzo[4,5]furo[2,3-d]pyrimidin-2-yl]butyric acid, cyclohexylamine salt, m.p. 205°.

Analogous reaction of
methyl 4-(4-chloro-5,6,7,8-tetrahydrobenzo[4,5]furo[2,3-d]pyrimidin-2-yl)butyrate with 3,4-methylenedioxybenzylamine followed by ester hydrolysis gives 4-[4-(3,4-methylenedioxybenzylamino)-5,6,7,8-tetrahydrobenzo[4,5]-furo[2,3-d]pyrimidin-2-yl]butyric acid, cyclohexylamine salt.

EXAMPLE 4

Preparation of 1-[4-(3-chloro-4-methoxybenzylamino)-5,6,7,8-tetrahydrobenzo[4,5]furo[2,3-d]pyrimidin-2-ylmethyl]piperidine-4-carboxylic acid

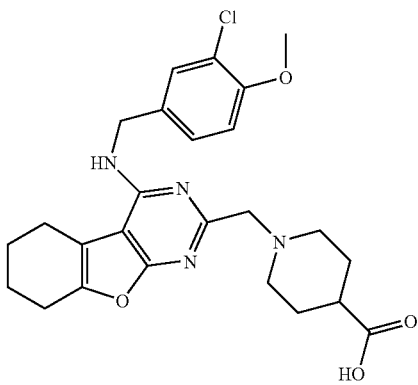

4.1 6.7 ml of POCl$_3$ are added dropwise with stirring and cooling to 6.2 ml of 2-chlorodimethylacetamide, and the mixture is stirred at room temperature for a further 10 minutes. 10.0 g of "BA" are added, and the mixture is stirred at 80° for a further 30 minutes. Conventional work-up gives 8.3 g of 4-chloro-2-chloromethyl-5,6,7,8-tetrahydrobenzo[4,5]furo-[2,3-d]pyrimidine ("DA") as an oil.

4.2 10 ml of ethyl piperidine-4-carboxylate are added to a solution of 8.3 g of "DA" in 100 ml of THF, and the mixture is stirred at room temperature for a further 16 hours. Water is added, and the mixture is extracted with methyl tert-butyl ether (MTB). The MTB extract ("X") is extracted with dilute HCl.

The HCl extract is rendered alkaline using dilute NaOH, extracted with MTB and subjected to conventional work-up, giving 2.9 g of ethyl 1-(4-chloro-5,6,7,8-tetrahydrobenzo[4,5]furo[2,3-d]pyrimidin-2-ylmethyl)-piperidine-4-carboxylate ("DB").

"X" contains the by-product ethyl 1-(2-chloromethyl-5,6,7,8-tetrahydrobenzo[4,5]furo[2,3-d]pyrimidin-4-yl)piperidine-4-carboxylate.

4.3 3.0 g of 3-chloro-4-methoxybenzylamine are added to a solution of 2.9 g of "DB" in 50 ml of 1-methyl-2-pyrrolidone, and the mixture is stirred over a steam bath for 1 hour. The mixture is subjected to conventional work-up, giving 2.9 g of ethyl 1-[4-(3-chloro-4-methoxybenzylamino)-5,6,7,8-tetrahydrobenzo[4,5]furo[2,3-d]pyrimidin-2-ylmethyl]piperidine-4-carboxylate ("DC"), m.p. 152°.

4.4 3 ml of NaOH (about 30%) are added to 2.8 g of "DC" in 30 ml of ethylene glycol monoethyl ether, and the mixture is stirred at 60° for a further 1 hour. The ether is removed, and the mixture is acidified to pH 4 using acetic acid. The crystals which deposit are washed with ice-water, giving 1.5 g of 1-[4-(3-chloro-4-methoxybenzylamino)-5,6,7,8-tetrahydrobenzo[4,5]furo[2,3-d]pyrimidin-2-ylmethyl]piperidine-4-carboxylic acid, m.p. 233-235°.

EXAMPLE 5

Preparation of 1-[4-(3-chloro-4-methoxybenzylamino)-5,6,7,8-tetrahydrobenzo[4,5]furo[2,3-d]pyrimidin-2-ylmethyl]-4-methylsulfonylpiperazine 5.1 2.85 g of ethyl piperazine-N-carboxylate are added dropwise to a solution of 4.7 g of "DA" and 1.8 g of triethylamine buffer substance f in 50 g of dichloromethane, and the mixture is stirred for a further 16 hours. The mixture is subjected to conventional work-up, giving 3.0 g of 1-(4-chloro-5,6,7,8-tetrahydrobenzo[4,5]furo[2,3-d]pyrimidin-2-ylmethyl)-4-ethoxycarbonylpiperazine ("EA") as an oil.

5.2 3.49 g of 3-chloro-4-methoxybenzylamine are added to a solution of 3.4 g of "EA" in 80 ml of 1,4-dioxane, and the mixture is stirred at 115° for 16 hours. The crystals which deposit and the solvent are separated off. 10 ml of 1-methyl-2-pyrrolidone are added to the residue, and the mixture is stirred at 115° for 1.5 hours. The mixture is subjected to conventional work-up, giving 3.25 g of 1-[4-(3-chloro-4-methoxybenzylamino)-5,6,7,8-tetrahydrobenzo[4,5]furo[2,3-d]pyrimidin-2-ylmethyl]-4-ethoxycarbonylpiperazine ("EB").

5.3 3.5 ml of 32% NaOH are added to a solution of 3.25 g of "EB" in 20 ml of ethylene glycol monoethyl ether, and the mixture is stirred at 110° for a further 5 hours. Conventional work-up gives 1.99 g of 1-[4-(3-chloro-4-methoxybenzylamino)-5,6,7,8-tetrahydrobenzo[4,5]furo[2,3-d]pyrimidin-2-ylmethyl]piperazine ("EC") as an oil.

5.4 520 mg of methanesulfonyl chloride are added dropwise to a solution of 2.0 g of "EC" and 360 mg of pyridine in 50 ml of dichloromethane, and the mixture is stirred at room temperature for a further 3 hours. Conventional work-up gives 1.0 g of 1-[4-(3-chloro-4-methoxybenzylamino)-5,6,7,8-tetrahydrobenzo[4,5]furo[2,3-d]pyrimidin-2-ylmethyl]-4-methylsulfonylpiperazine, dihydrochloride.

EXAMPLE 6

Preparation of 4-[4-(3-chloro-4-methoxybenzylamino)-9H-1,3,9-triazafluoren-2-yl]butyric acid

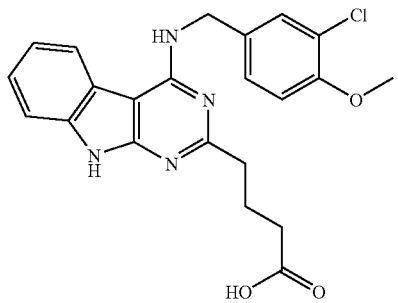

6.1 Ammonia is passed into 350 ml of cold THF for 30 minutes. 30 g of methyl 4-chlorocarbonylbutyrate are then added dropwise, with ammonia continuing to be passed in at the same time. The crystals which deposit are separated off, and the residue is boiled a number of times with ethyl acetate. The combined filtrates are distilled off, and the residue is recrystallised from ethyl acetate, giving 23.4 g of methyl 4-aminocarbonylbutyrate ("FA"), m.p. 80°.

6.2 15 ml of oxalyl chloride are added dropwise at from −2 to 0° to a solution of 15 ml of DMF in 300 ml of acetonitrile, and the mixture is stirred for a further 30 minutes. 23.25 g of "FA" are added dropwise at a maximum of 0°, and, after the mixture has been stirred for 15 minutes, 29 ml of pyridine are added dropwise. Ether is added, and the mixture is subjected to conventional work-up, giving 20 g of methyl 4-cyanobutyrate ("FB") as an oil.

6.3 A solution of 180 ml of methyl cyanoacetate in 300 ml of DMF is added dropwise at 0-50° with stirring and under a nitrogen atmosphere to a solution of 88 g of NaH suspension in 2 litres of DMF. The mixture is stirred for a further 30 minutes without cooling. A solution of 106 ml of o-fluoronitrobenzene in 100 ml of DMF is subsequently added dropwise, and the mixture is stirred at room temperature for a further 14 hours. The mixture is acidified using 10% HCl and subjected to conventional work-up, giving 165 g of methyl cyano(2-nitrophenyl)acetate ("FC"), m.p. 58-60°.

6.4 A solution of 74 g of "FC" in 180 ml of acetic acid and 550 ml of toluene is heated to 80°. 130 g of zinc powder are added in portions with stirring and while noting the temperature (80-85°), and the mixture is stirred at room temperature for a further 14 hours. Conventional work-up gives 30 g of 2-amino-3-methoxycarbonylindole ("FD"), m.p. 136°.

6.5 HCl is passed into a solution of 4.0 g of "FD" and 2.8 g of "FB" in 60 ml of 1,4-dioxane for 2 hours with stirring and at a maximum of 30°. The solution is left to stand for 48 hours. Conventional work-up gives 1.4 g of methyl 2-[(4-methoxycarbonylbutyrimidoyl)amino]-1H-indole-3-carboxylate ("FE"), m.p. 95°,

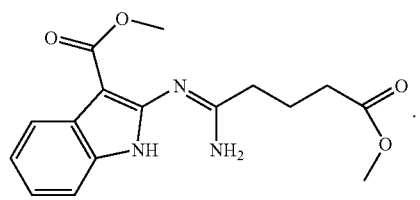
"FE"

6.6 1.4 g of "FE" are added to 50 ml of acetic acid, and the mixture is stirred on a steam bath for 1 hour and subjected to conventional work-up, giving 1.0 g of methyl 4-(4-oxo-4,9-dihydro-3H-1,3,9-triazafluoren-2-yl)butyrate ("FF"), m.p. 258°,

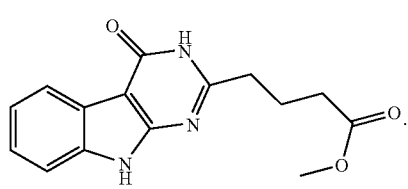
"FF"

6.7 1.0 g of "FF" is refluxed for 3 hours with 40 ml of POCl₃. After the POCl₃ has been removed, the residue is treated 2× with dichloromethane, giving 1.0 g of methyl 4-(4-chloro-9H-1,3,9-triazafluoren-2-yl)butyrate ("FG"), m.p. 258°,

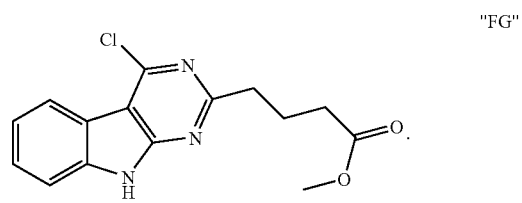
"FG"

6.8 A solution of 1.0 g of "FG" and 1.0 g of 3-chloro-4-methoxybenzylamine in 30 ml of 1-methyl-2-pyrrolidone is heated to 180°. After the solvent has been removed, the mixture is recrystallised from n-butanol, giving 0.45 g of methyl 4-[4-(3-chloro-4-methoxybenzylamino)-9H-1,3,9-triazafluoren-2-yl]butyrate ("FH").

6.9 A solution of 0.35 g of "FH" and 10 ml of 2N NaOH in 20 ml of methanol is heated on a steam bath for 1 hour. The methanol is removed, water is added, the mixture is acidified using HCl, and the product is separated off, giving 300 mg of 4-[4-(3-chloro-4-methoxybenzylamino)-9H-1,3,9-triazafluoren-2-yl]butyric acid, m.p. 258°.

The acid is dissolved in methanol, and 2 drops of ethanolamine are added. Diethyl ether is added, and the crystals which deposit are isolated, giving 280 mg of 4-[4-(3-chloro-4-methoxybenzylamino)-9H-1,3,9-triazafluoren-2-yl]butyric acid, ethanolamine salt, m.p. 143°.

Analogous reaction of methyl 4-cyanobenzoate instead of "FB" gives the following compound
4-[4-(3-chloro-4-methoxybenzylamino)-9H-1,3,9-triazafluoren-2-yl]benzoic acid, sodium salt, m.p.>250°.

The following compounds are obtained analogously
4-[4-(3,4-methylenedioxybenzylamino)-9H-1,3,9-triazafluoren-2-yl]butyric acid,
4-(4-benzylamino-9H-1,3,9-triazafluoren-2-yl)butyric acid,
4-[4-(3,4-dimethoxybenzylamino)-9H-1,3,9-triazafluoren-2-yl]butyric acid,
4-[4-(3,4-dichlorobenzylamino)-9H-1,3,9-triazafluoren-2-yl]butyric acid,
4-{4-[(pyridin-3-ylmethyl)amino]-9H-1,3,9-triazafluoren-2-yl}butyric acid,
4-[4-(3-chloro-4-methoxybenzylamino)-9H-1,3,9-triazafluoren-2-yl]valeric acid,
4-[4-(3,4-methylenedioxybenzylamino)-9H-1,3,9-triazafluoren-2-yl]valeric acid,
4-(4-benzylamino-9H-1,3,9-triazafluoren-2-yl)butyric acid,
4-[4-(3,4-dimethoxybenzylamino)-9H-1,3,9-triazafluoren-2-yl]valeric acid,
4-[4-(3,4-dichlorobenzylamino)-9H-1,3,9-triazafluoren-2-yl]valeric acid,
4-{4-[(pyridin-3-ylmethyl)amino]-9H-1,3,9-triazafluoren-2-yl}valeric acid,
4-[4-(3-chloro-4-methoxybenzylamino)-9H-1,3,9-triazafluoren-2-yl]cyclohexanecarboxylic acid,
4-[4-(3,4-methylenedioxybenzylamino)-9H-1,3,9-triazafluoren-2-yl]cyclohexanecarboxylic acid,
4-(4-benzylamino-9H-1,3,9-triazafluoren-2-yl)butyric acid,
4-[4-(3,4-dimethoxybenzylamino)-9H-1,3,9-triazafluoren-2-yl]cyclohexanecarboxylic acid,
4-[4-(3,4-dichlorobenzylamino)-9H-1,3,9-triazafluoren-2-yl]cyclohexanecarboxylic acid,
4-{4-[(pyridin-3-ylmethyl)amino]-9H-1,3,9-triazafluoren-2-yl}cyclohexanecarboxylic acid,
4-[4-(3-chloro-4-methoxybenzylamino)-9H-1,3,9-triazafluoren-2-yl]benzoic acid, 4-[4-(3,4-methylenedioxybenzylamino)-9H-1,3,9-triazafluoren-2-yl]benzoic acid, 4-(4-benzylamino-9H-1,3,9-triazafluoren-2-yl)benzoic acid, 4-[4-(3,4-dimethoxybenzylamino)-9H-1,3,9-triazafluoren-2-yl]benzoic acid, 4-[4-(3,4-dichlorobenzylamino)-9H-1,3,9-triazafluoren-2-yl]benzoic acid, 4-{4-[(pyridin-3-ylmethyl)amino]-9H-1,3,9-triazafluoren-2-yl}benzoic acid.

EXAMPLE 7

Preparation of 4-[4-(3,4-methylenedioxybenzylamino)-9-ethyl-9H-1,3,9-triazafluoren-2-yl]benzoic acid 7.1 448 g of NaH are introduced into 9 l of DMF, then 967 g of cyanoacetamide are added in portions over the course of 1 hour at 2-8° with strong ice cooling and under a nitrogen atmosphere. The mixture is stirred for a further 30 minutes, 600 ml of 1-fluoro-2-nitrobenzene are added, and the mixture is stirred for a further 2 hours. The mixture is poured into 50 l of ice-water, acidified using 3 l of conc. HCl and subjected to further conventional work-up, giving 956 g of 2-cyano-2-(2-nitrophenyl)acetamide ("GA"), m.p. 172-174°.

7.2 Analogously to Example 6.4, 956 g of "GA" give 352 g of 2-amino-3-aminocarbonylindole ("GB").

7.3 13 g of NaH are suspended in 500 ml of DMF. A solution of 52.6 g of "GB" in 200 ml of DMF is subsequently added dropwise with stirring at 0°. 26 ml of iodoethane in 100 ml of DMF are then added dropwise at 0°, and the mixture is stirred for a further 1 hour. The mixture is subjected to conventional work-up, giving 67.9 g of 2-amino-3-aminocarbonyl-1-ethylindole ("GC").

7.4 A solution of 10.0 g of "GC", 8.0 g of methyl 4-formylbenzoate and 9.4 g of sodium disulfite in 100 ml of N,N-dimethylacetamide is stirred at 160° for 7 hours. Conventional work-up gives 4.8 g of methyl 4-(9-ethyl-4-oxo-4,9-dihydro-3H-1,3,9-triazafluoren-2-yl)benzoate ("GD").

7.5 5 ml of DMF are added dropwise to a solution of 4.8 g of "GD" in 100 ml of thionyl chloride. The batch is left to stand for 60 hours. Conventional work-up gives 3.9 g of methyl 4-(4-chloro-9-ethyl-9H-1,3,9-triazafluoren-2-yl)benzoate ("GE").

7.6 A solution of 2.4 g of "GE" and 2 ml of piperonylamine in 5 ml of 1-methyl-2-pyrrolidone is stirred at a bath temperature of 110° for 2 hours. Conventional work-up gives 2.7 g of methyl 4-[4-(3,4-methylenedioxybenzylamino)-9-ethyl-9H-1,3,9-triazafluoren-2-yl]benzoate ("GF").

7.7 Treatment of 2.6 g of "GF" with 5 ml of NaOH (about 32%) in 10 ml of ethylene glycol monoethyl ether gives 2.4 g of 4-[4-(3,4-methylenedioxybenzylamino)-9-ethyl-9H-1,3,9-triazafluoren-2-yl]benzoic acid, sodium salt, m.p.>250°.

Analogous reaction of "GE" with 3-chloro-4-methoxybenzylamine followed by ester hydrolysis gives 4-[4-(3-chloro-4-methoxybenzylamino)-9-ethyl-9H-1,3, 9-triazafluoren-2-yl]benzoic acid, sodium salt, m.p.>250°.

EXAMPLE 8

Preparation of 4-[4-(3-chloro-4-methoxybenzylamino)-9-methyl-9H-1,3,9-triazafluoren-2-yl]benzoic acid 8.1 A solution of 38 g of "GB", 36.1 g of methyl 4-formylbenzoate and 41.8 g of sodium disulfite in 200 ml of N,N-dimethylacetamide is stirred at 140° for 3 hours. The product crystallises out, and washing gives 30 g of methyl 4-(4-oxo-4,9-dihydro-3H-1,3,9-triazafluoren-2-yl)benzoate ("HA"), m.p.>250°.

8.2 30 ml of DMF are added dropwise to a solution of 10 g of "HA" in 100 ml of thionyl chloride. The batch is left to stand for 16 hours. Conventional work-up gives 8.5 g of methyl 4-(4-chloro-9H-1,3,9-triazafluoren-2-yl)benzoate ("HB").

8.3 400 mg of NaH (suspension) are added to a solution of 3.2 g of "HB" in 50 ml of DMF, the mixture is stirred for 1 hour, 2 ml of iodomethane are subsequently added, and the mixture is stirred for a further 1 hour. Conventional work-up gives 3.0 g of methyl 4-(4-chloro-9-methyl-9H-1,3,9-triazafluoren-2-yl)benzoate ("HC").

8.4 Analogously to Example 7.6, reaction of 1.5 g of "HC" with 3-chloro-4-methoxybenzylamine gives 1.0 g of methyl 4-[4-(3-chloro-4-methoxybenzylamino)-9-methyl-9H-1,3,9-triazafluoren-2-yl]benzoate ("HD"), m.p. 205-206°.

8.5 Ester hydrolysis of "HD" analogously to Example 7.7 gives 4-[4-(3-chloro-4-methoxybenzylamino)-9-methyl-9H-1,3,9-triazafluoren-2-yl]benzoic acid, sodium salt, m.p.>250°.

Analogous reaction of "HC" with 3,4-methylenedioxybenzylamine followed by ester hydrolysis gives 4-[4-(3,4-methylenedioxybenzylamino)-9-methyl-9H-1,3, 9-triazafluoren-2-yl]benzoic acid, sodium salt, m.p.>250°.

Analogous reaction of "GB" with methyl 5-formylpentanoate, chlorination, methylation, reaction with 3-chloro-4-methoxybenzylamine and ester hydrolysis gives 5-[4-(3-chloro-4-methoxybenzylamino)-9-methyl-9H-1,3, 9-triazafluoren-2-yl]pentanoic acid, potassium salt.

Analogous reaction of "HB" with benzyl bromide, reaction with 3-chloro-4-methoxybenzylamine followed by ester hydrolysis gives 4-[4-(3-chloro-4-methoxybenzylamino)-9-benzyl-9H-1,3,9-triazafluoren-2-yl]benzoic acid, sodium salt, m.p.>250°.

Analogous reaction of "HB" with 2-iodopropane, reaction with 3-chloro-4-methoxybenzylamine followed by ester hydrolysis gives 4-[4-(3-chloro-4-methoxybenzylamino)-9-isopropyl-9H-1, 3,9-triazafluoren-2-yl]benzoic acid, sodium salt, m.p.>250°.

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with pump mechanism. The solution can be sprayed into the mouth or nose. One spray shot (about 0.1 ml) corresponds to a dose of about 0.14 mg.

The invention claimed is:

1. A compound of formula I

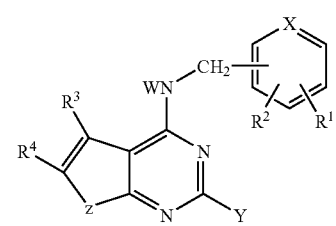

in which $R^1$ and $R^2$ are each, independently of one another, H, A, OH, OA or Hal, $R^1$ and $R^2$ together are alternatively alkylene having 3-5 carbon atoms, —O—$CH_2$—$CH_2$—, —$CH_2$—O—$CH_2$—, —O—$CH_2$—O— or —O—$CH_2$—$CH_2$—O—, $R^3$ and $R^4$ together are —$(CH_2)_3$—, —$(CH_2)_4$— or —CH=CH—CH=CH—, W is H or alkyl having 1, 2, 3 or 4 carbon atoms, X is CH or N, Y is $(CH_2)_q$—$R^7$ or $R^5$, $R^6$ or $R^9$, each of which is unsubstituted or monosubstituted by $(CH_2)_n R^{20}$, Z is O, NH or NA', A' is alkyl having 1-6 carbon atoms, —CHAr or —CHAr-A", A" is alkyl having 1-6 carbon atoms, $R^5$ is linear or branched alkyl having 1-10 carbon atoms, in which one or two $CH_2$ groups may be replaced by —CH=CH— groups, —C≡C— groups, —O—, CO, —S—, —SO—, $SO_2$, —NH— or —NA—, $R^6$ is cycloalkyl or cycloalkylalkylene having 5-12 carbon atoms, $R^7$ is a saturated or unsaturated 5-7-membered heterocyclic radical having 1-4 N, O or S atoms which is unsubstituted or monosubstituted, disubstituted or trisubstituted by $R^{20}$, A, Hal or $CF_3$, $R^9$ is Ar or $(CH_2)_k$—Ar, $R^{20}$ is —COOH, —COOA, —$CONH_2$, —CONHA, —$CONA_2$, —CN, tetrazol-5-yl, —$S(O)_m A$, —$S(O)_m NH_2$ or —$S(O)_m OH$,

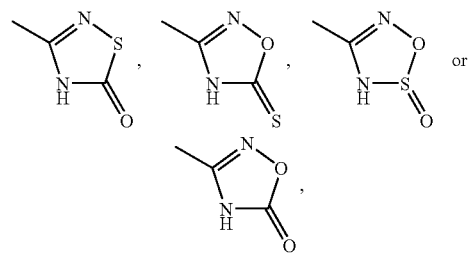

A is alkyl or alkenyl having from 1 to 6 carbon atoms, in which 1-7 H atoms may be replaced by F,
Ar is a phenyl radical which is unsubstituted or monosubstituted, disubstituted or trisubstituted by Hal, A, OA, OH, $SO_2NH_2$, $SO_2NHA$, $SO_2NA_2$ or CN,
Hal is F, Cl, Br or I,
k and q are each, independently of one another, 0, 1, 2, 3 or 4,
m is 1 or 2 and
n is 0, 1, 2 or 3,
or a pharmaceutically acceptable salt, stereoisomer, or mixture thereof.

2. A compound according to claim 1, wherein
X is CH,
or a pharmaceutically acceptable salt, stereoisomer, or mixture thereof.

3. A compound according to claim 1, wherein
$R^9$ is a phenyl radical which is unsubstituted or monosubstituted or disubstituted by COOH, COOA, $CONH_2$, $CONA_2$, CONHA, CN, $NHSO_2A$, $N(SO_2A)_2$ or $SO_2A$,
or a pharmaceutically acceptable salt, stereoisomer, or mixture thereof.

4. A compound according to claim 1, wherein
Y is phenyl, 1-piperidinyl, piperazinyl or cyclohexyl, each of which is monosubstituted or disubstituted by COOH, COOA or —$S(O)_mA$,
or a pharmaceutically acceptable salt, stereoisomer, or mixture thereof.

5. A compound according to claim 1, wherein
$R^3$ and $R^4$ together are —$(CH_2)_3$—, —$(CH_2)_4$— or —CH=CH—CH=CH—,
$R^1$ and $R^2$ are each, independently of one another, H, OA or Hal,
$R^1$ and $R^2$ together are alternatively alkylene containing —$CH_2$—O—$CH_2$—,
Y is phenyl, 1-piperidinyl, piperazinyl or cyclohexyl, each of which is monosubstituted or disubstituted by COOH, COOA which is monosubstituted or disubstituted by COOH, COOA or —$S(O)_mA$,
or a pharmaceutically acceptable salt, stereoisomer, or mixture thereof.

6. A compound according to claim 1, wherein
Y is cyclopentylmethylene, cyclohexylmethylene, cyclohexylethylene, cyclohexylpropylene or cyclohexylbutylene, each of which is monosubstituted by COOH or COOA,
or a pharmaceutically acceptable salt, stereoisomer, or mixture thereof.

7. A compound according to claim 1, wherein
Y is $R^5$ or $R^6$, each of which is substituted by COOH, COOA, $CONH_2$, $CONA_2$, CONHA or —$S(O)_mA$,
or a pharmaceutically acceptable salt, stereoisomer, or mixture thereof.

8. A compound according to claim 1, wherein
Y is $R^5$, $R^6$ or $R^9$, each of which is substituted by —$(CH_2)_n$—$R^{20}$,
$R^5$ is methyl, ethyl, propyl or butyl,
$R^9$ is phenyl or benzyl,
n is 0 or 1
$R^{20}$ is COOH, COOA, $CONH_2$, $CONA_2$, CONHA or —$S(O)_mA$,
or a pharmaceutically acceptable salt, stereoisomer, or mixture thereof.

9. A compound according to claim 1, wherein
X is CH,
Y is $R^5$, $R^6$ or $R^9$, each of which is substituted by —$(CH_2)_n$—$R^{20}$,
$R^5$ is methyl, ethyl, propyl or butyl,
$R^9$ is phenyl or benzyl,
n is 0 or 1,
$R^{20}$ is COOH or COOA,
or a pharmaceutically acceptable salt, stereoisomer, or mixture thereof.

10. A compound according to claim 1, wherein
X is CH,
Y is $R^5$, $R^6$ or $R^9$, each of which is substituted by —$(CH_2)_n$—$R^{20}$,
Z is NH or NHA',
$R^5$ is methyl, ethyl, propyl or butyl,
$R^9$ is phenyl or benzyl,
n is 0 or 1,
$R^{20}$ is COOH or COOA,
or a pharmaceutically acceptable salt, stereoisomer, or mixture thereof.

11. A compound according to claim 1, wherein
X is CH,
Y is $R^5$, $R^6$ or $R^9$, each of which is substituted by —$(CH_2)_n$—$R^{20}$,
Z is O,
$R^5$ is methyl, ethyl, propyl or butyl,
$R^9$ is phenyl or benzyl,
n is 0 or 1,
$R^{20}$ is COOH or COOA,
or a pharmaceutically acceptable salt, stereoisomer, or mixture thereof.

12. A compound according to claim 1, wherein
$R^1$ and $R^2$ are each, independently of one another, H, A, OH, OA or Hal,
$R^1$ and $R^2$ together are alternatively alkylene having 3-5 carbon atoms, —O—$CH_2$—$CH_2$—, —$CH_2$—O—$CH_2$—, —O—$CH_2$—O— or —O—$CH_2$—$CH_2$—O—,
$R^3$ and $R^4$ together are —$(CH_2)_3$—, —$(CH_2)_4$— or —CH=CH—CH=CH—,
W is H,
X is CH or N,
Y is $(CH_2)_q$—$R^7$, or $R^5$, $R^6$ or $R^9$, each of which is unsubstituted or monosubstituted by $(CH_2)_nR^{20}$,
Z is O, NH or NA',
A' is alkyl having 1-6 carbon atoms, —CHAr or —CHAr-A",
A" is alkyl having 1-6 carbon atoms,
$R^5$ is linear or branched alkyl having 1-10 carbon atoms,
$R^6$ is cycloalkyl or cycloalkylalkylene having 5-12 carbon atoms,
$R^7$ is a saturated or unsaturated, 5-7-membered heterocyclic radical having 1-2 N atoms which is unsubstituted or monosubstituted by $R^{20}$, A, Hal or $CF_3$,
$R^9$ is Ar or $(CH_2)_k$—Ar,
$R^{10}$, $R^{11}$,
$R^{12}$ and $R^{13}$ are H,
$R^{20}$ is —COOH, —COOA or —$S(O)_mA$,
A is alkyl having from 1 to 6 carbon atoms, in which 1-7 H atoms may be replaced by F,
Ar is phenyl,
Hal is F, Cl, Br or I
k and q are each, independently of one another, 0, 1, 2, 3 or 4, m is 1 or 2 and n is 0, 1, 2 or 3, or a pharmaceutically acceptable salt, stereoisomer, or mixture thereof.

13. Compounds of the formula I according to claim 1,

4-[4-(3-chloro-4-methoxybenzylamino)-9-(1-phenylethyl)-6,7,8,9-tetrahydro-5H-1,3,9-triazafluoren-2-yl]benzoic acid, 4-[4-benzylamino-9-(1-phenylethyl)-6,7,8,9-tetrahydro-5H-1,3,9-triazafluoren-2-yl]benzoic acid, 4-[4-(3,4-dimethoxybenzylamino)-9-(1-phenylethyl)-6,7,8,9-tetrahydro-5H-1,3,9-triazafluoren-2-yl]benzoic acid, 4-[4-(3,4-dichlorobenzylamino)-9-(1-phenylethyl)-6,7,8,9-tetrahydro-5H-1,3,9-triazafluoren-2-yl]benzoic acid, 4-[4-(3,4-methylenedioxybenzylamino)-9-(1-phenylethyl)-6,7,8,9-tetrahydro-5H-1,3,9-triazafluoren-2-yl]benzoic acid, 4-[4-(3-chloro-4-methoxybenzylamino)-9-(1-phenylethyl)-6,7,8,9-tetrahydro-5H-1,3,9-triazafluoren-2-yl]butyric acid, 4-[4-benzylamino-9-(1-phenylethyl)-6,7,8,9-tetrahydro-5H-1,3,9-triazafluoren-2-yl]butyric acid, 4-[4-(3,4-dimethoxybenzylamino)-9-(1-phenylethyl)-6,7,8,9-tetrahydro-5H-1,3,9-triazafluoren-2-yl]butyric acid, 4-[4-(3,4-dichlorobenzylamino)-9-(1-phenylethyl)-6,7,8,9-tetrahydro-5H-1,3,9-triazafluoren-2-yl]butyric acid, 4-[4-(3,4-methylenedioxybenzylamino)-9-(1-phenylethyl)-6,7,8,9-tetrahydro-5H-1,3,9-triazafluoren-2-yl]butyric acid, 4-[4-(3,4-methylenedioxybenzylamino)-5,6,7,8-tetrahydrobenzo[4,5]furo[2,3-d]pyrimidin-2-yl]benzoic acid, 4-[4-(3-chloro-4-methoxybenzylamino)-5,6,7,8-tetrahydrobenzo[4,5]furo[2,3-d]pyrimidin-2-yl]benzoic acid, 4-(4-benzylamino-5,6,7,8-tetrahydrobenzo[4,5]furo[2,3-d]pyrimidin-2-yl)benzoic acid, 4-[4-(3,4-dimethoxybenzylamino)-5,6,7,8-tetrahydrobenzo[4,5]furo[2,3-d]pyrimidin-2-yl]benzoic acid, 4-[4-(3,4-dichlorobenzylamino)-5,6,7,8-tetrahydrobenzo[4,5]furo[2,3-d]pyrimidin-2-yl]benzoic acid, 4-{4-[(pyridin-3-ylmethyl)amino]-5,6,7,8-tetrahydrobenzo[4,5]-furo[2,3-d]pyrimidin-2-yl}benzoic acid, 4-[4-(3-chloro-4-methoxybenzylamino)-5,6,7,8-tetrahydrobenzo[4,5]furo[2,3-d]pyrimidin-2-yl]butyric acid, 4-[4-(3,4-methylenedioxybenzylamino)-5,6,7,8-tetrahydrobenzo[4,5]furo[2,3-d]pyrimidin-2-yl]butyric acid, 1-[4-(3-chloro-4-methoxybenzylamino)-5,6,7,8-tetrahydrobenzo[4,5]furo[2,3-d]pyrimidin-2-ylmethyl]piperidine-4-carboxylic acid, 1-[4-(3-chloro-4-methoxybenzylamino)-5,6,7,8-tetrahydrobenzo[4,5]furo[2,3-d]pyrimidin-2-ylmethyl]piperazine, 1-[4-(3-chloro-4-methoxybenzylamino)-5,6,7,8-tetrahydrobenzo[4,5]furo[2,3-d]pyrimidin-2-ylmethyl]-4-methylsulfonylpiperazine, 4-[4-(3-chloro-4-methoxybenzylamino)-9H-1,3,9-triazafluoren-2-yl]butyric acid, 4-[4-(3-chloro-4-methoxybenzylamino)-9H-1,3,9-triazafluoren-2-yl]benzoic acid, 4-[4-(3,4-methylenedioxybenzylamino)-9-ethyl-9H-1,3,9-triazafluoren-2-yl]benzoic acid, 4-[4-(3-chloro-4-methoxybenzylamino)-9-ethyl-9H-1,3,9-triazafluoren-2-yl]benzoic acid, 4-[4-(3-chloro-4-methoxybenzylamino)-9-methyl-9H-1,3,9-triazafluoren-2-yl]benzoic acid, 4-[4-(3,4-methylenedioxybenzylamino)-9-methyl-9H-1,3,9-triazafluoren-2-yl]benzoic acid, 5-[4-(3-chloro-4-methoxybenzylamino)-9-methyl-9H-1,3,9-triazafluoren-2-yl]pentanoic acid, 4-[4-(3-chloro-4-methoxybenzylamino)-9-benzyl-9H-1,3,9-triazafluoren-2-yl]benzoic acid, 4-[4-(3-chloro-4-methoxybenzylamino)-9-isopropyl-9H-1,3,9-triazafluoren-2-yl]benzoic acid, and pharmaceutically usable derivatives, solvates and stereoisomers thereof.

14. A process for the preparation of a compound of formula I according to claim 1, or a salt thereof, comprising reacting a) a compound of the formula II

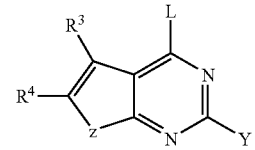

in which

Y, Z, $R^1$ and $R^2$ are as defined in claim 1, and L is Cl, Br, OH, $SCH_3$ or a reactive esterified OH group, with a compound of formula III

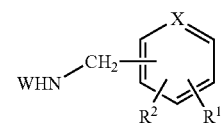

in which

X, W, $R^1$ and $R^2$ are as defined in claim 1, or b) converting a radical X in a compound of formula I into another radical X by, hydrolyzing an ester group to give a COOH group or converting a COOH group into an amide or a cyano group, and/or converting a compound of formula I into a salt thereof.

15. A pharmaceutical composition comprising at least one compound of formula I according to claim 1 or a salt, or mixture thereof, and a pharmaceutically acceptable carrier.

16. A method for the treatment of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, female sexual disorders, inflammation, osteoporosis, malign hypertonia, phaeochromacytoma, peripheral vascular (occlusion) diseases, vascular diseases, thrombocytopenia, ulcus pepticum, peristaltic motion disorders, percutaneous transluminal coronary angioplasty, carotid angioplasty, postoperative stenosis of the coronary bypass, premonitory pains or benign prostate hyperplasia, comprising administering to a host in need thereof a compound according to claim 1, or a salt, stereoisomer, or mixture thereof.

17. A method for the treatment of a diseases of the cardiovascular system and/or therapy of a potency disorder, comprising administering to a host in need thereof a compound according to claim 1, or a salt, stereoisomer, or mixtuer thereof.

18. A composition according to claim 15, further comprising at least one additional medicament active ingredient.

19. A composition according to claim 18, wherein the additional medicament active ingredient is
  a) a prostaglandin,
  b) calcium antagonist,
  c) antithrombotic,
  d) endothelin receptor antagonist,
  e) nitrate,
  f) α-adrenergic inhibitor,
  g) centrally acting dopaminergic active ingredient,
  h) ACE inhibitor,
  i) NEP inhibitor,
  j) mixed α,β-inhibitor,
  k) vasoactive intestinal peptide.

20. A kit consisting of a separate pack of
  (a) an effective amount of a compound of formula I according to claim 1 and/or a pharmaceutically acceptable salt, stereoisomer or mixture thereof, and of
  (b) an effective amount of an additional medicament active ingredient.

* * * * *

UNITED STATES PATENT AND TRADEMARK OFFICE
CERTIFICATE OF CORRECTION

| | | |
|---|---|---|
| PATENT NO. | : 7,312,224 B2 | Page 1 of 1 |
| APPLICATION NO. | : 10/491680 | |
| DATED | : December 25, 2007 | |
| INVENTOR(S) | : Michael-Hans Eggenweiler | |

It is certified that error appears in the above-identified patent and that said Letters Patent is hereby corrected as shown below:

Column 39, line 3 reads "mixtuer" should read -- mixture --

Column 40, line 4 should have "or" at the end.

Signed and Sealed this

Twenty-seventh Day of October, 2009

David J. Kappos
*Director of the United States Patent and Trademark Office*